(12) United States Patent
Rebec et al.

(10) Patent No.: US 9,839,360 B2
(45) Date of Patent: Dec. 12, 2017

(54) SYSTEMS, METHODS, AND APPARATUSES FOR MONITORING END STAGE RENAL DISEASE

(71) Applicant: BioMetric Holdings, Inc., Portland, OR (US)

(72) Inventors: Mihailo V. Rebec, Bristol, IN (US); Slavko N. Rebec, Bristol, IN (US); Richard G. Sass, Portland, OR (US); Mihailo R. Rebec, Bristol, IN (US)

(73) Assignee: Optica, Inc., Tigard, OR (US)

( * ) Notice: Subject to any disclaimer, the term of this patent is extended or adjusted under 35 U.S.C. 154(b) by 564 days.

(21) Appl. No.: 13/892,166

(22) Filed: May 10, 2013

(65) Prior Publication Data
US 2013/0303865 A1   Nov. 14, 2013

Related U.S. Application Data

(60) Provisional application No. 61/645,971, filed on May 11, 2012.

(51) Int. Cl.
| | |
|---|---|
| *A61M 1/14* | (2006.01) |
| *A61B 5/1455* | (2006.01) |
| *A61B 5/00* | (2006.01) |
| *A61M 1/16* | (2006.01) |
| *A61B 5/145* | (2006.01) |
| *A61B 5/1459* | (2006.01) |
| *A61B 5/20* | (2006.01) |
| *A61B 5/103* | (2006.01) |

(52) U.S. Cl.
CPC .......... *A61B 5/0082* (2013.01); *A61B 5/0013* (2013.01); *A61B 5/1459* (2013.01); *A61B 5/14532* (2013.01); *A61B 5/201* (2013.01); *A61M 1/1601* (2014.02); *A61B 5/0022* (2013.01); *A61B 5/1032* (2013.01); *A61B 5/14546* (2013.01); *A61B 2560/045* (2013.01)

(58) Field of Classification Search
CPC ... A61B 5/0022; A61B 5/0082; A61B 5/1459; A61B 5/14532; A61B 5/14546; A61B 5/1032; A61M 1/1601; A61M 1/1603; A61M 1/1692; A61M 1/3403; A61M 1/3607; A61M 1/3609
See application file for complete search history.

(56) References Cited

U.S. PATENT DOCUMENTS

| | | |
|---|---|---|
| 2005/0221276 A1 | 10/2005 | Rozakis |
| 2006/0222567 A1 | 10/2006 | Kloepfer |

(Continued)

*Primary Examiner* — Eric Winakur
(74) *Attorney, Agent, or Firm* — Schwabe Williamson & Wyatt, P.C.

(57) ABSTRACT

An end stage renal disease (ESRD) monitoring system may include an implantable sensor and a reader device with an optical sensor. The implantable sensor may be configured to detect a group of analytes relevant to ESRD, such as glucose, creatinine, urea, and potassium. The implantable sensor may be implanted into the dermis of an animal, and may exhibit color changes in response to the presence of the target analytes or reaction product(s) thereof. The reader device may be configured to capture an image of the implanted sensor and to determine the concentration of the target analytes based at least in part on the image. The reader device may be a personal electronic device such as a cell phone, PDA, or personal computer.

26 Claims, 14 Drawing Sheets

(56) References Cited

U.S. PATENT DOCUMENTS

| | | |
|---|---|---|
| 2009/0124875 A1 | 5/2009 | Bentsen |
| 2010/0167283 A1 | 7/2010 | Horgan |
| 2011/0251493 A1* | 10/2011 | Poh .................... G06K 9/00255 600/477 |
| 2011/0256024 A1 | 10/2011 | Cole |
| 2013/0215244 A1* | 8/2013 | Mestha .................. G06T 5/003 348/77 |

\* cited by examiner

FIGURE 8

| Reference Ranges (Analyte) | | |
|---|---|---|
| Gender | Age (yrs) | Reference Range (RR) |
| Male | 1-2 | 0.1-0.4 mg/dl |
| Male | 3-4 | 0.1-0.5 mg/dl |
| Male | 5-9 | 0.2-0.6 mg/dl |
| Male | 10-11 | 0.3-0.7 mg/dl |
| Male | 12-13 | 0.4-0.8 mg/dl |
| Male | 14-15 | 0.5-0.9 mg/dl |
| Male | 16-70 | 0.8-1.3 mg/dl |
| Female | 1-3 | 0.1-0.4 mg/dl |
| Female | 4-5 | 0.2-0.5 mg/dl |
| Female | 6-8 | 0.3-0.6 mg/dl |
| Female | 9-15 | 0.4-0.7 mg/dl |
| Female | 16-70 | 0.6-1.1 mg/dl |

SYSTEMS, METHODS, AND APPARATUSES FOR MONITORING END STAGE RENAL DISEASE

TECHNICAL FIELD

Embodiments herein relate to the field of medical devices and systems, and, more specifically, to devices and systems for managing end stage renal disease.

BACKGROUND

Long-term monitoring of medical conditions such as diabetes presents challenges for both patients and medical care providers. Traditional methods that require the patient to repeatedly obtain and test blood or other fluids can be painful and inconvenient, and this may lead to reduced compliance on the part of the patient.

Implantable sensors developed to mitigate these drawbacks have been expensive, bulky, require a power source or specialized reader, or lack the necessary mechanical strength to remain functional within the patient for extended periods of time. In addition, such sensors may be difficult to remove several weeks after implantation.

A large number of people with diabetes have end stage renal disease (ESRD). ESRD can also develop as a result of chronic hypertension, polycystic kidney disease, and a number of other conditions, and can dramatically affect lifespan and quality of life in diabetic patients. However, very little is being done at present to manage this condition, which requires frequent monitoring of renal function. The monitoring of renal function is especially problematic in patients receiving dialysis treatments, which can result in low blood analyte concentrations and blood test results that are difficult to interpret accurately. While the dialysate from the patient can be tested for some analytes, this type of testing may not properly reflect the concentration of creatinine and BUN still residing in the body. There is no acknowledged analysis system available that can be used to determine the toxin state of the body before, during and after dialysis. For these reasons, it can be very difficult to monitor the health of ESRD patients. Poor disease management is a primary factor in the relatively short survival time of patients diagnosed with ESRD.

BRIEF DESCRIPTION OF THE DRAWINGS

Embodiments will be readily understood by the following detailed description in conjunction with the accompanying drawings. Embodiments are illustrated by way of example and not by way of limitation in the figures of the accompanying drawings.

FIG. 8 illustrates an example of a reference table that provides creatinine ranges by age and gender, all in accordance with various embodiments.

DETAILED DESCRIPTION OF DISCLOSED EMBODIMENTS

Figure 1A:
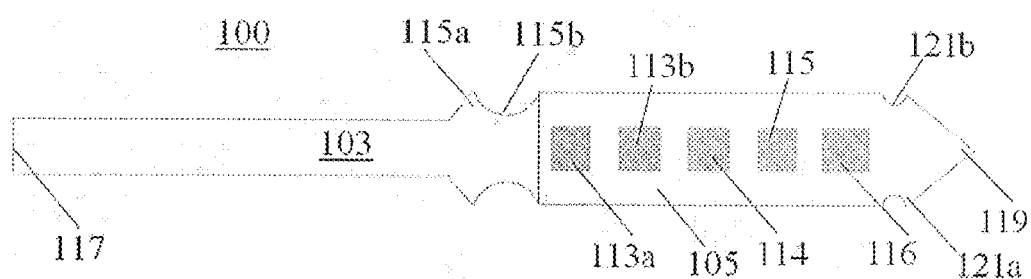
FIGS. 1a-e illustrate plan views of an implantable ESRD analyte sensor in accordance with various embodiments.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "NB" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous, and are generally intended as "open" terms (e.g., the term "including" should be interpreted as "including but not limited to," the term "having" should be interpreted as "having at least," the term "includes" should be interpreted as "includes but is not limited to," etc.).

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

Very little monitoring is currently done for individuals in ESRD. Embodiments described herein provide methods, apparatuses, and systems to monitor analytes related to kidney function. Monitoring these analytes may enable healthcare professionals to monitor the condition of ESRD patients, schedule dialysis treatments or other treatments when they are needed, and/or to adapt the conditions of the treatment to the individual patient for an optimal treatment outcome.

Typically, analyte monitoring of ESRD patients is limited to testing a sample of the patient's blood or dialysate for BUN or creatinine. However, interstitial fluid may provide a more reliable measure of analyte concentration than blood and dialysate in patients receiving dialysis treatments. Therefore, implantable sensors may be used to more accurately monitor the health of ESRD patients than traditional blood/dialysate testing methods.

In one embodiment, a monitoring system and method may be used to monitor an individual in any of stages I, II, III, IV, or V of renal disease. The system and method may be used to determine whether the individual should begin dialysis, when the individual should begin dialysis, and/or one or more parameters of a dialysis treatment for the individual (e.g., flow rate or duration of treatment).

In another embodiment, a monitoring system and method may be used to monitor an individual with renal disease and to alert the individual of an impending or immediate need for dialysis, based on the concentrations of one or more analytes in the interstitial fluid of the individual.

In another embodiment, a monitoring system and method may be used to monitor an individual treated with peritoneal dialysis (e.g., at the individual's home or in a health care facility) and to determine one or more parameters of the peritoneal dialysis based at least on the concentration of one or more analytes in the interstitial fluid of the individual. In some examples, the monitoring system and method may indicate to the individual or a caretaker a duration of time for which the peritoneal dialysis should continue, when the dialysate should be emptied, or another parameter of the peritoneal dialysis procedure.

In another embodiment, a monitoring system may communicate directly or indirectly with a dialysis machine (e.g., through an operator of the dialysis machine) to adjust flow rate, duration of dialysis, or another parameter based at least on a determined/calculated concentration of one or more analytes in the interstitial fluid of a user. In some examples, a monitoring system may be used with smaller home hemodialysis systems, and may help the ESRD patient and their primary care assisting person to determine when the dialysis machine should be hooked up, how fast the flow rates should be, and/or when to stop the dialysis. This would be especially useful for overnight dialysis sessions. The sensor monitoring system may communicate directly with the dialysis unit to adjust dialysis rates for optimal operation and to shut off dialysis, and may alarm the user to decouple the home hemodialysis system.

Glucose, creatinine, BUN, and potassium are examples of analytes that can be used to monitor the status and progression of ESRD. Each of these analytes affects, or is affected by, the disease. Maintaining tight control over glucose levels can help slow the progression of the degradation in kidney function. Creatinine and BUN concentrations are indicators of the kidney function initially, to help determine when dialysis needs to be started, and to manage the dialysis process after dialysis has begun. Potassium can be impacted significantly by renal failure, and maintaining potassium levels within a well controlled range is critical to the overall function of the body.

Embodiments herein provide methods, systems, and apparatuses for monitoring ESRD in an animal, such as a human. An ESRD monitoring system may include an analyte sensor and a reader device. In some examples, the analyte sensor may be an implantable analyte sensor. An implantable ESRD sensor and a reader device may be used to monitor several analytes that are directly related to renal function. Implantable sensors as described herein may be more robust, more easily optically read, thinner, less expensive to produce, and/or more easily removed than prior known implantable sensors. A personal electronic device with an optical sensor, such as a cell phone, tablet computing device, personal digital assistant, or laptop, can be used as the reader device. Thus, the sensor user's existing personal electronic device can be used to read the sensor, eliminating the need for a dedicated reader. This further reduces the expense and increases the convenience of the monitoring system.

For the purposes of this description, an "implantable sensor" is a sensor that is implanted into the skin with the main body of the sensor, or a portion thereof, residing in the dermis of the skin. In some embodiments, the entirety of the implanted sensor may reside in the dermis. In other embodiments, a portion of the implanted sensor may protrude into the epidermis, extending through the outer surface or to just below the surface of the skin. The sensor or a portion thereof may be implanted to a depth of 20 μm to 200 μm below the surface of the skin. The implantable sensor may reside in the skin for a period of time that can range from one hour to a couple of years depending upon one or more factors, such as the type(s) of analysis needed and the stability of the analysis components. The implantable sensor may be inserted and/or removed with an insertion/removal device.

In one embodiment, an implantable sensor may have a base, a body defining one or more chambers, and one or more permeability/blocking members. The base may be constructed from one or more materials such as a polymer or a metal. The body may be coupled to a surface of the base. The chambers may be one or more gaps, wells, or voids extending partially or fully through the thickness of the body. An analyte reagent system with one or more sensor reagents may be retained within a chamber. The analyte reagent system may include one or more sensor reagents configured to detect the target analyte(s). One or more permeability/blocking members may be coupled to the chambers and/or to the body. Some or all of the sensor reagents may be retained on or between the permeability/blocking member(s), or between the permeability/blocking member(s) and the body.

The analyte reagent system may be configured to respond to the presence of an analyte by changing color and/or emitting light (luminescence). In some embodiments, the analyte reagent system may be configured to respond to the presence of an analyte by a reduction in emitted light in a portion of the sensor. A sensor may include one or more analysis regions, each configured to exhibit a color or emission of light in the presence of a corresponding analyte. An analysis region may be configured to detect a target analyte relevant to ESRD, such as glucose, creatinine, urea or blood urea nitrogen (BUN), and/or potassium. A sensor may have one, two, three, four, or more than four analysis regions. Some sensors may include at least one analysis region configured to detect creatinine, at least one analysis region configured to detect BUN, and/or at least one analysis region configured to detect potassium. Other sensors may include an analysis region configured to detect glucose. A sensor may include analysis regions configured to detect one, two, three, or all four of BUN, creatinine, potassium, and glucose. Optionally, some sensors may include an analysis region configured to detect another target analyte, such as a drug.

In some embodiments, a sensor may include two or more analysis regions configured to detect a target analyte within different concentration ranges (e.g., one detects the analyte within a "high" concentration range and another detects the same analyte within a "low" concentration range). Some or all of the analysis regions may detect different analytes and/or have different detection ranges (i.e., configured to detect analytes within different concentration ranges), but may exhibit responses within a common range of response. Thus, a particular color in one analysis region may indicate that a first analyte is present at a first concentration, and the same color in another analysis region may indicate a different concentration of the same analyte, or a different analyte. Likewise, two analysis regions may be configured to exhibit different colors in response to the same concentration of the same analyte.

The sensor may include one or more control regions configured to provide a reference color, current, shape, or other parameter for use by the reader device. A control region may be an analysis region that is configured to detect a target analyte (e.g., a duplicate analysis region) or to detect a non-target analyte. Other control regions may be control elements located on or within the sensor. Control elements may be, but are not limited to, a fixed color and/or shape that can be used by the reader device as a reference. Such control regions may be provided to confirm sensor integrity, for calibration of the reader device based on implantation depth or dermal characteristics, for detection of leakages or malfunction, to orient a captured image for analysis, to assess implantation depth or sensor integrity, to determine optical corrections for differences in ambient light or light intensity, skin pigmentation/color, skin scattering, or image exposure/collection times, and/or to correct a representative value or other calculated value based on differences in the depth of the sensor in the skin (e.g., for a sensor that is placed at a greater or lesser depth in the skin than recommended).

The response or color of each analysis/control region may be read by a reader device such as mobile electronic device (e.g., a wireless phone or computer) that includes an optical sensor (e.g., a camera). The reader device may capture an image of the implanted sensor. The reader device may then determine the concentrations of one or more of the target analytes based on the captured image. The reader device may determine one or more representative values, such as a blood glucose value, that represents the determined concentration. The image, image data, or representative value(s) may be communicated by the reader device to the user, a caretaker, a medical care provider, a medical device manufacturer, a health management system, a satellite health/device management system, and/or a medical device such as a dialysis machine.

Systems, methods, and apparatuses disclosed herein may allow patients, caretakers, device manufacturers, health management systems, and/or medical services providers to monitor the progression of ESRD, to more accurately determine when dialysis should be initiated, and how frequently dialysis should be done. The concentration data can also be used to determine or set optimal flow rates during dialysis. In addition, embodiments disclosed herein may allow medical device manufacturers to monitor the quality of the data or information delivered to a patient, caretaker, or medical service provider, to monitor and track sensor performance, to create and update performance logs for sensors, to change or update an algorithm of the reader device based on sensor performance (e.g., to compensate for changes in sensor responses as a result of sensor aging or deterioration), to determine or predict a recommended time or date for sensor removal or replacement, and/or to communicate relevant data regarding sensor performance to a user, caretaker, medical services provider, health management system, or other entity or system. Sensors as described herein may be configured to monitor the concentration of a target analyte within the dermis of a user for 30, 60, 90, 180, or more than 180 days (e.g., 1 year, 1.5 years, or 2 years). The sensors may also be used to monitor the functionality of the dialysis equipment. For example, data from a sensor could be used to determine whether there is a blockage in the lines of a dialysis system, or a malfunction in the dialysis process, and to alert an equipment operator at a dialysis site or the equipment manufacturers (e.g., of a home dialysis system).

Closer monitoring of ESRD and efficient adjustment of these parameters may significantly improve the quality and duration of the ESRD patient's life. In patients with renal disease in stages I-IV, such monitoring may contribute to earlier diagnosis of ESRD and may help to delay the onset of ESRD by allowing the individuals to better control glucose levels and/or other factors that contribute to the advance of the disease. In patients with renal disease in stages IV-V who have not begun dialysis, the systems and methods described herein may be used to determine when the individuals should begin dialysis, and under what conditions. For patients receiving peritoneal dialysis at home, systems and methods described herein may improve treatment outcomes by allowing the treatment to be tailored to the individual receiving it. In some embodiments, systems and methods described herein may be used to automatically control a medical device, such as a dialysis machine, based at least on the concentration of one or more analytes in a subject's interstitial fluid. Overall, embodiments of the present disclosure may help to delay the onset of ESRD and need for dialysis treatments, increase the efficacy of dialysis treatments, reduce morbidity and mortality in patients with renal disease, and extend the life expectancy of an ESRD patient.

Examples of Implantable ESRD Sensors

In various embodiments, implantable ESRD sensors may be provided with multiple analysis regions in various arrangements and configurations. In some embodiments, implantable ESRD sensors may be provided in different configurations for use by corresponding subpopulations of individuals with ESRD. In one embodiment, some configurations may be configured for use by individuals with ESRD and diabetes, and other configurations may be adapted for use by individuals with ESRD who do not have diabetes (e.g., individuals who have hypertension). In some embodiments, an ESRD analyte sensor configured for use by individuals with diabetes may include reagents/reagent systems operable to detect glucose and one or more analytes that are relevant to kidney function (e.g., BUN, creatinine, potassium, and/or pH). In other embodiments, an implantable ESRD sensor may include reagents/reagent systems operable to detect any one or more of BUN, creatinine, potassium, and/or pH. In some embodiments, an ESRD analyte sensor may be configured to detect two, three, or all four of BUN, creatinine, potassium, and pH. Optionally, some ESRD analyte sensors may lack reagents/reagent systems for detecting glucose (e.g., for use in subjects with ESRD who do not have diabetes). Other ESRD analyte sensors may be configured to detect glucose in addition to BUN, creatinine, potassium, and/or pH (e.g., for use in subjects with ESRD who have diabetes).

In some embodiments, an ESRD sensor may be provided with one or more additional analysis regions configured to detect a non-target analyte (e.g., to assess local tissue conditions around the analyte sensor), to exhibit a response to an analyte within a particular concentration range, and/or to serve as a duplicate of another analysis region (e.g., for confirmation of analyte concentration reading and/or confirmation of analyte sensor stability/performance).

FIGS. 1a-e illustrate plan views of implantable ESRD analyte sensors in accordance with various embodiments. FIGS. 2a-c illustrate side views of an implantable ESRD sensor as shown in FIG. 1a, and FIGS. 2d-e illustrate side views of an implantable ESRD sensor as shown in FIGS. 2d-e, all in accordance with various embodiments.

As illustrated, an implantable ESRD sensor 100 may have a base 103 coupled to a body 105. Analysis regions 113a, 113b, 114, 115, and 116 may be arranged along base 103 and surrounded by body 105. In some embodiments, a first analysis region 113a may be configured to detect glucose concentrations within a first range, such as 20 to 250 µg/dl. A second analysis region 113b may be configured to detect glucose concentrations within a second range, such as from 200 to 450 µg/dl. A third analysis region 114 may be configured to detect creatinine. A fourth analysis region 115 may be configured to detect blood urea nitrogen (BUN). A fifth analysis region 116 may be configured to detect potassium. Some ESRD sensors may include an analysis region that detects changes in pH. In some embodiments, glucose-detecting analysis regions may be omitted.

Optionally, an implantable ESRD sensor may include one or more control regions. Control regions may allow calibration of the reader device and/or confirmation of sensor positioning, sensor malfunction, and/or accessibility of implantable sensor 100 to the target analyte(s) or control analyte(s). Some control regions may be configured to detect a non-target analyte or another parameter such as pH. A non-target analyte may be one that is typically present at relatively constant levels within the dermis (e.g., sodium, uric acid, chloride, or cholesterol. Examples of such control regions are shown in FIGS. 1a and 1e (control regions 102).

Other control regions may be control elements that are not configured to detect an analyte, but are provided as a reference for the use of the reader device and/or user. Control elements may include, but are not limited to, fixed colors/shapes that are located in or on the implantable sensor. Examples of control elements are shown in FIG. 1d (control elements 299) and FIG. 1e (control element 198). Control elements 299 or 198, or other markings/shapes, may be used by a reader device to orient a captured image of the sensor after sensor implantation. Control elements 299 and/or 198 may have a fixed color that can be used by the reader device to correct for variations in skin tone, implantation depth, or other factors.

Some control regions may be duplicate analysis regions. FIG. 1e illustrates a sensor configuration in which each analysis region and the control region 102 are included in duplicate. Duplicate analysis regions may be read by the reader device, and the reader device may compare the obtained values. Based on the comparison, the reader device may disregard one of the values, average the values to determine the analyte concentration, and/or detect a potential leakage or sensor malfunction.

An analysis region may include a chamber (see e.g., FIGS. 2a-c) and an analyte reagent system within the chamber. In some embodiments, an analysis region may also include the underlying base, surrounding body, and/or one or more permeability/blocking member(s). Thus, a first chamber may be part of a first analysis region, a second chamber may be part of a corresponding second analysis region, and a third chamber may be part of a corresponding third analysis region. Alternatively, a chamber may represent two or more analysis regions. For example, a sensor may have a single continuous chamber with a configuration that varies from one side of the chamber to another due to differences in the concentrations of reagents, base thicknesses, or different optical properties of the base.

Base 103 and body 105 may form first and second layers, respectively, of implantable sensor 100 (see FIG. 2a). Alternatively, body 105 and base 103 may be formed as integral portions of a single unit (see FIG. 2b). For example, body 105 and base 103 may be a single piece formed by molding, thermoforming, vacuum forming, compaction and sintering, cutting, or extrusion of a base material. Base 103 may have an elongate shape with a first end 117 and an opposite second end 119. Second end 119 may terminate in a point or other shape to aid penetration into the skin during implantation or subsequent removal of the sensor from the skin. Base 103 may include one or more surface or edge features configured to enhance the retention of implantable sensor 100 within the dermis after implantation. In the examples of FIG. 1a, implantable sensor 100 includes projections 115a and 121a near a first end and a second opposite end, respectively, of body 105. Invaginations 115b and 121b are positioned between the projections and body 105. These features may provide resistance to backward-directed pulling forces to prevent the dislocation of the implantable sensor after implantation.

In some embodiments, second end 119 may be inserted into the dermis of an animal and first end 117 may be retained externally, above the epidermis, for removal. For example, the terminal edge (e.g., 0.5 mm) of first end 117 may protrude from the surface of the skin. In other embodiments, first end 117 may be positioned within the epidermis a short distance below the outer surface of the skin, and may become exposed for removal 1, 2, 3, 4, 5, or 6 months after implantation. In still other embodiments, first end 117 may be positioned below the epidermis after implantation. First end 117 may alternatively be positioned within the epidermis and may become exposed by natural exfoliation of the epidermis over a period of weeks or months. As another alternative, first end 117 may be inserted into the dermis of an animal and second end 119 may be retained externally (above the epidermis), within the epidermis, or below the epidermis as described above.

Figure 1B:
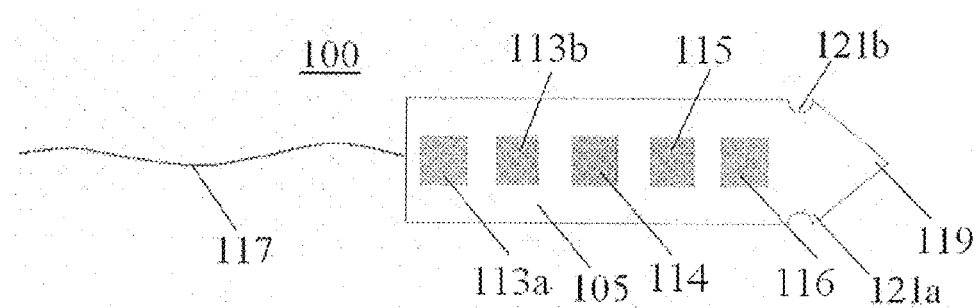
Figure 1C:
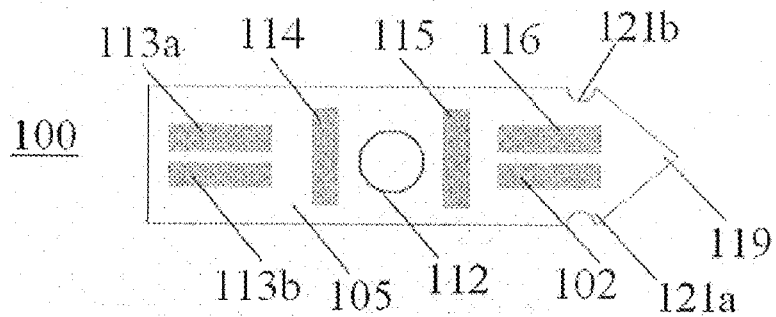
Figure 1D:
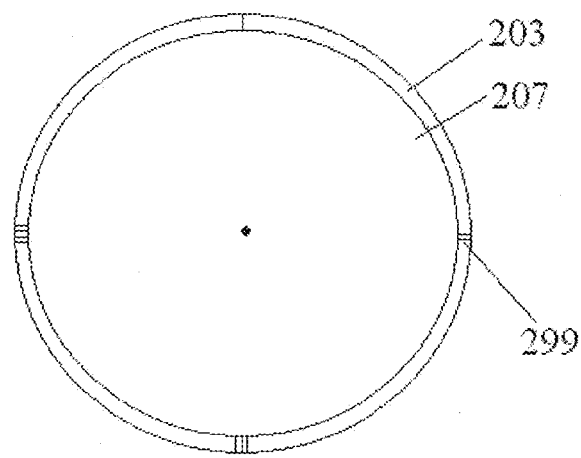
Figure 1E:
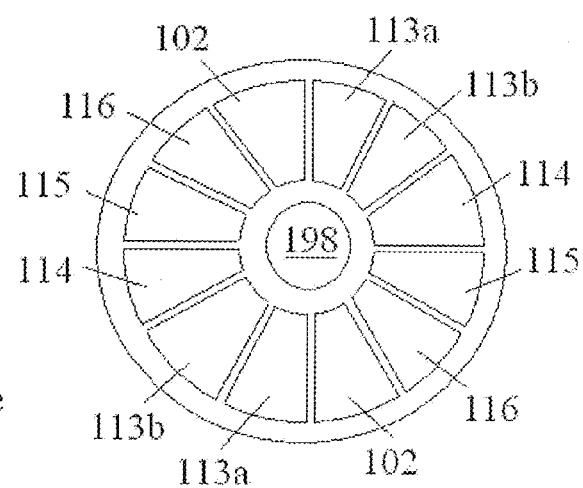
Figure 2A:
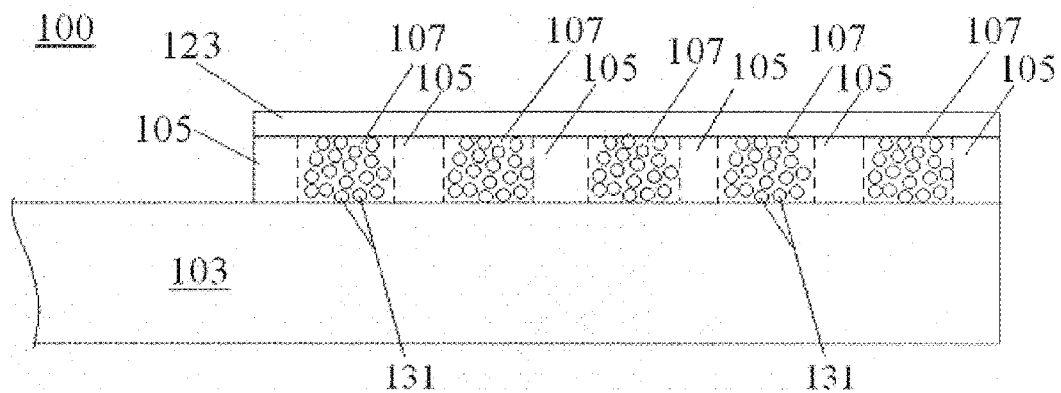
FIGS. 2a-c and 2d-e illustrate side views of an implantable ESRD analyte sensor as shown in FIGS. 1a and 1d, respectively.
Figure 2B:
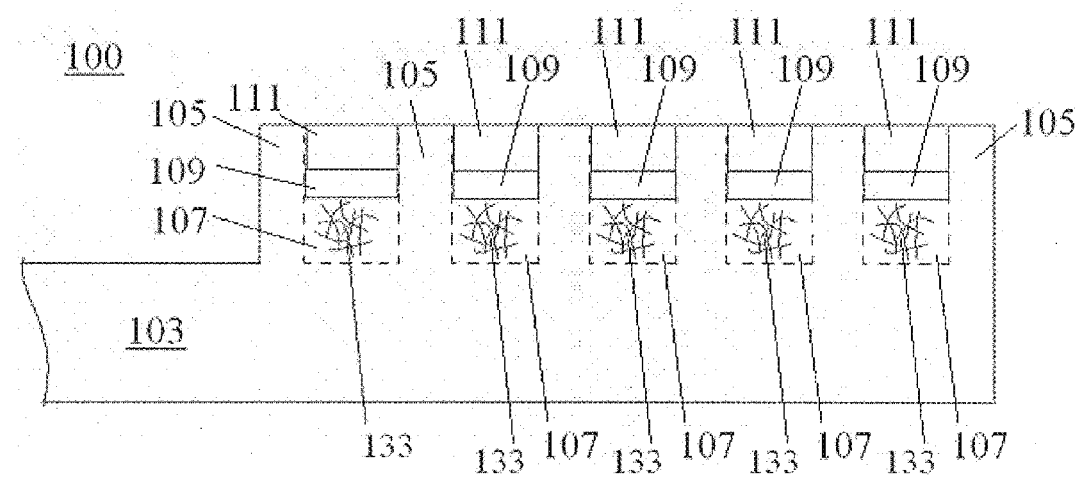
Figure 2C:
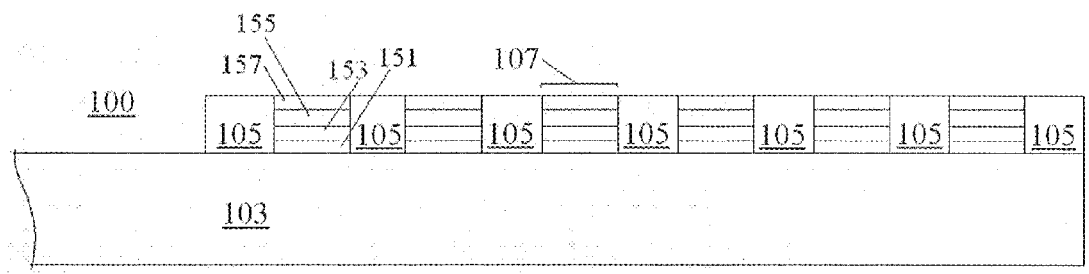
Figure 2D:
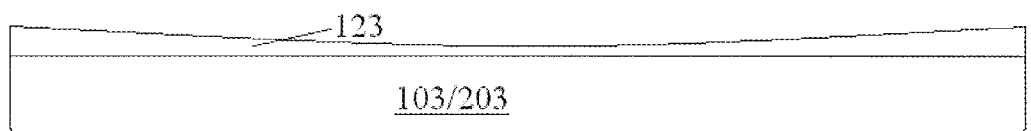
Figure 2E:
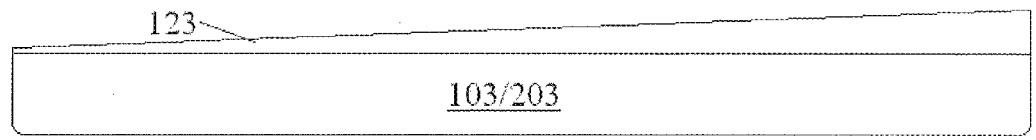

As shown in FIG. 1b, first end 117 may be a relatively thin and flexible member, such as a narrow tape or string, which can be grasped and pulled to remove the sensor from the skin. Other sensors may lack an elongated end. Optionally, sensors may have a surface feature configured to mate with a portion of a removal device for removal of the sensor. For example, as shown in FIG. 1c, a sensor may be provided with a hole 112 through a portion of the base and/or body. A portion of an insertion/removal device may be inserted through the hole and pulled to remove the sensor from the skin. The sensor may be configured to at least partially fold or collapse for removal. Some sensors may have a pointed or narrow end to aid in removal of the sensor from the dermis.

Base 103 can include one or more materials such as a metal and/or metal alloy (e.g., stainless steel), a hydrogel, a plastic or polymer, a biopolymer (e.g., a polyanhydride), ceramic, and/or silicon. Examples of plastics or polymers may include, but are not limited to, polyacrylic acid (PAA), cross-linked polyethylene (PEX, XLPE), polyethylene (PE), polyethylene terephthalate (PET, PETE), polyphenyl ether (PPE), polyvinyl chloride (PVC), polyvinylidene chloride (PVDC), polylactic acid (PLA), polypropylene (PP), polybutylene (PB), polybutylene terephthalate (PBT), polyamide (PA), polyimide (PI), polycarbonate (PC), polytetrafluoroethylene (PTFE), polystyrene (PS), polyurethane (PU), polyester (PEs), acrylonitrile butadiene styrene (ABS), poly(methyl methacrylate) (PMMA), polyoxymethylene (POM), polysulfone (PES), styrene-acrylonitrile (SAN), ethylene vinyl acetate (EVA), and styrene maleic anhydride (SMA). In one embodiment, base 103 may be magnetic. For example, base 103 may comprise 50-90% iron. In some embodiments, base 103 may comprise magnetic/magnetized stainless steel. In some examples the stainless steel can be a stainless steel of either the martensitic type or the ferritic type.

Base 103 may have a thickness in the range of 30 µm to 500 µm. For example, base 103 may have a thickness in the range of 30-35 µm, 35-40 µm, 40-50 µm, 50-60 µm, 60-70 µm, 70-80 µm, 80-100 µm, 100-150 µm, 150-200 µm, 200-250 µm, 250-300 µm, 300-350 µm, 350-400 µm, 400-450 µm, or 450-500 µm.

In some sensors, ambient light may be reflected by reagents within chambers 107, and the resulting diffuse reflection signal may be measured by a reader device. Optionally, base 103 may include a reflective material that is integral (i.e., integrated within the material used to form base 103) or provided in the form of a coating along one or more surfaces of base 103, such as a coating along the bottom surface. The inclusion of reflective materials in or on base 103 may reduce background effects from tissue below the sensor and/or enhance the reflection or transflection of light from by the sensor. At least some ambient light may pass through the reagents within chambers 107 to be reflected by the reflective material of base 103. The resulting transflectance signal may be measured by a reader device. In such examples, the sensor may provide diffuse reflection signals and/or transflectance signals, and the reader may measure the signals of one or both types. In one example, base 103 includes a strip of polyimide material impregnated with titanium dioxide ($TiO_2$). Optionally, base 103 may be thicker at a first end than at a second, opposite end, to provide an optical gradient.

Body 105 may be constructed from a variety of materials depending on the strength and permeability desired. In some examples, body 105 may be a plastic or a polymer (e.g., polyimide). Body 105 may range in thickness from 5 µm to 500 µm thick. For example, body 105 may have a thickness in the range of 5-10 µm, 10-15 µm, 15-20 µm, 20-25 µm, 25-30 µm, 30-35 µm, 35-40 µm, 40-45 µm, 45-50 µm, 50-60 µm, 60-70 µm, 70-80 µm, 80-100 µm, 100-150 µm, 150-200 µm, 200-250 µm, 250-300 µm, 300-350 µm, 350-400 µm, 400-450 µm, or 450-500 µm. In one example, base 103 is a strip of polyimide material impregnated with $TiO_2$, and body 105 is polyurethane.

Body 105 can be applied onto base 103 as a liquid solution or vapor by printing, roll-coating, dip-coating, spin coating, spraying, chemical/physical vapor deposition, sol-gel, or other known methods. In some examples, the solution or vapor may be applied indiscriminately to an area of base 103. A pattern mask or other physical/chemical blocking agent may be used to prevent deposition of the solution or vapor over the areas where chambers 107 are desired. In other examples, the solution may be applied selectively to some areas of base 103, leaving other areas (e.g., chambers 107 and/or first end 117) untreated. Alternatively, body 105 may be a pre-formed solid, semi-solid, or gel, and may be coupled to base 103 with an adhesive. In some embodiments, body 105 and base 103 are formed as a single unit. Base 103 and/or body 105 can have varying thicknesses.

As best viewed in FIGS. 2a-c, one or more chambers 107 may extend partially or entirely through the thickness of body 105. Chambers 107 may be cut from body 105 before or after body 105 is applied or coupled to base 103. Alternatively, body 105 and base 103 may be a single unit, and chambers 107 may be made during formation of the unit (e.g., as part of a molding process) or after formation of the unit (e.g., by cutting or otherwise removing material from the unit).

The number, shape, depth, and spatial arrangement of chambers 107 may vary among embodiments. Similarly, the shape and depth of chambers 107 may vary within an individual sensor, with some chambers having a greater depth or different shape than others. An implantable sensor may have 2, 3, 4, 5, 6, 7, 8, 9, 10, or more than 10 chambers 107. In one example (FIG. 1a), the implantable sensor has six rectangular areas (i.e., chambers 107) that may be, for example, 300×400 µm in size. In other embodiments, one or more of chambers 107 may be round, oblong, polygonal, and/or have one or more tapered sides.

At least some of chambers 107 may contain an analyte reagent system with one or more sensor reagents, discussed further below with reference to FIG. 3. Sensor reagents may be bound to microscopic beads, fibers, membranes, gels, or other matrices in various combinations. Some sensor reagents may be retained between membranes, bound to membrane materials coated onto a membrane, or coupled/immobilized to a hydrophilic matrix. The analyte reagent system may be provided in a single layer or in multiple layers. For example, an analyte reagent system may include two, three, four, five, six, seven, eight, nine, ten, or more than ten layers.

At least one of the layers may be permeability/blocking member, such as a membrane or gel that is selectively permeable to one or more sensor reagents, analytes, or reaction products. A permeability/blocking member may include one or more membranes and/or gels, alone or in combination. Examples of permeability/blocking members are described in U.S. Pat. No. 7,964,390, which is hereby incorporated by reference in its entirety. Permeability/blocking members may include one or more membranes, such as cellulose acetate membranes, cellulose acetate phosphate membranes, cellulose acetate phthalate membranes, and/or polyurethane membranes. Some permeability/blocking members may include, for example, a hydrogel, polyurethane, polyvinylpyrrolidone, acrylic polyesters, vinyl resins, fluorocarbons, silicones, rubbers, chitosan, hydroxyethylmethacrylate (HEMA), and/or polyhydroxyethylmethacrylate.

One or more of the layers may comprise a liquid or gel. In some embodiments, the liquid (or a liquid component of the gel) may be provided by the surrounding tissue after implantation of the sensor. For example, a layer may include one or more gel components in a dehydrated form, such as a powder, that is configured to form a gel upon exposure to tissue fluids.

FIG. 2d illustrates an embodiment of a sensor with a multi-layer analyte reagent system. In this embodiment, the analyte reagent system includes a first layer 151, a second layer 153, and a third layer 157.

First layer 151 may include a matrix and an indicator. The matrix may include one or more of a liquid, a gel, beads, fibers, a membrane or membrane component(s), and/or another porous material. Some of the sensor reagents may be dispersed in the matrix or bound to a component thereof. The indicator may be a group of sensor reagents configured to collectively provide a response, such as a color change, upon exposure to a target analyte.

An indicator may be a pH sensitive dye that produces a color change in response to a change in pH resulting from a target analyte or reaction product/intermediate. The indicator may return to its previous color when the pH returns to its previous level. An indicator may include a group of chemical species that function as a system. For example, an indicator may include one or more of an ionophore, a lipophilic anion, and a chromoionophore (i.e., a lipophilic hydrogen ion sensitive dye). The ionophore may extract the ion to be detected (e.g., hydrogen), causing the chromoionophore to change color. Electrical neutrality may be maintained by the negatively charged anion. For example, as illustrated in FIG. 3, an indicator may include a chromogen, an ionophore, and a lipophilic anion. In other embodiments, an indicator may be a luminescent reagent that emits light in response to a target analyte or reaction product/intermediate. Luminescent reagents may include, but are not limited to, photoluminescent (e.g., phosphorescent or fluorescent), chemiluminescent, electroluminescent, electrochemiluminescent, or bioluminescent reagents. Alternatively, an indicator may be an enzyme or reaction product thereof. Some embodiments may include two or more indicators in the same or different analysis regions.

In some examples, the matrix may be a membrane and the first group of sensor reagents may be immobilized on the membrane. In other examples, at least some of the sensor reagents of the indicator may be bound to a matrix component, such as beads 131 (FIG. 2a) or elements 133 (e.g., fibers, a membrane, a membrane component, or other porous material; FIG. 2b). Different sensor reagents may be bound to separate membranes, beads, or other matrix components, or to different portions of a single membrane, bead, or matrix component.

Second layer 153 may be coupled to first layer 151. Second layer 153 may include a detection reagent. A detection reagent is a reagent that reacts with, or catalyzes a reaction of, the target analyte to produce a reaction product or intermediate. A detection reagent may be an enzyme or an enzyme system. For example, a detection reagent for glucose detection may be glucose oxidase ("GOX"), and a detection reagent for lactose detection may be lactase. In some embodiments, a detection reagent may be or include an antibody that binds to an analyte or reaction product, and/or an enzyme attached to such an antibody. The binding of the antibody to the analyte or reaction product may cause a change in the activity of the enzyme, which may influence or cause a change in pH. Thus, an analyte reagent system can include any antibody, enzyme, antibody-enzyme complex, or indicator known in the art for use in the detection of analytes in vitro or in vivo.

Second layer 153 may include a liquid, a gel, beads, fibers, a membrane or membrane component(s), and/or another porous material. In some examples, second layer 153 may include a membrane that is selectively permeable to a target analyte. The membrane may be impermeable to one or more sensor reagents (e.g., detection/indicator reagents). A detection reagent may be immobilized on a membrane, beads, or other element of second layer 153.

Third layer 157 may be a permeability/blocking member that is configured to selectively limit the passage of a target analyte or interfering compounds into second layer 153. Optionally, a fourth layer 155 may be applied to reduce or prevent damage to another layer during manufacturing. For example, fourth layer 155 may be a protective layer applied over first layer 151, and second layer 153 may be applied over fourth (protective) layer 155. This may protect first layer 151 from being damaged as second layer 153 is being applied. In some examples, fourth layer 155 may also be a permeability/blocking member such as a membrane or gel. Optionally, fourth layer 155 and/or an additional layer may be applied over some or all of the analyte sensor to enhance biocompatibility, structural integrity, or both. For example, in some embodiments an analyte sensor may include an outer layer/coating of a biocompatible material. In some embodiments, the biocompatible material may be applied to the analyte sensor by dip coating or vapor coating. Examples of suitable biocompatible materials include, but are not limited to, nafion, phosphorylcholines, polyurethane with phospholipids, and hydrogels.

Figure 3:
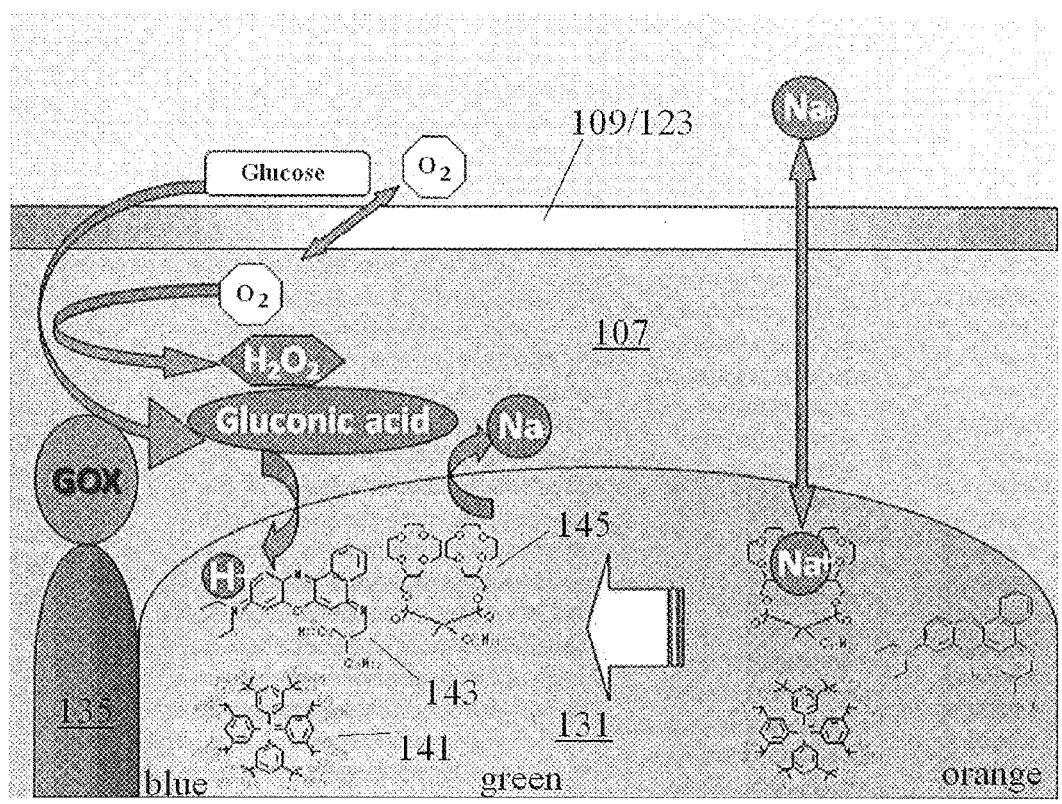
FIG. 3 illustrates an example of a reagent system for glucose detection in an implantable ESRD sensor.

In other embodiments, some or all of the detection reagent(s) and indicator(s) may be provided within a single layer (see e.g., FIGS. 2a, 2b, and 3). The indicator and detection reagent may be immobilized within the layer on beads, membranes, fibers, or other elements. A permeability/blocking member 109 may be coupled to the chambers 107 and/or to the body 105, and the detection reagent and indicator may be retained between the permeability/blocking member 109 and the body 105. In some examples, the detection reagent and/or indicator may be bound to the underside of the permeability/blocking member 109. Permeability/blocking member 109 may include one, two, or more two layers of membrane and/or gel. Optionally, a second permeability/blocking member 111 may be added over first permeability/blocking member 109.

Permeability/blocking members of varying configurations may be used among chambers 107 to provide increased or decreased permeability to the target analyte(s) among neighboring chambers 107. For example, a first permeability/blocking member 109 of a first chamber 107 may be more or less permeable to a target analyte than a permeability/blocking member 109 of a second chamber 107. One or more of the permeability/blocking members may be configured for a desired permeability to a control analyte, such as sodium or cholesterol. Permeability/blocking members may be applied individually to chambers 107 as separate units. Alternatively, permeability/blocking member 123 may be coupled to multiple chambers 107 as a single unit, as shown in FIG. 2a.

In some embodiments, individual permeability/blocking members 109 may be coupled to corresponding chambers 107, and a single permeability/blocking member 123 may be applied as a single layer across the upper surface of body 105 (see FIG. 2b). Permeability/blocking member 123 may have different configurations at different locations along its length, such as differences in pore size(s), thickness, or other parameters. This may provide one or more chambers with different permeabilities to a target analyte or reagent (see e.g., FIGS. 2d-e).

One or more of the permeability/blocking members and chambers may be made of a set of materials with a composition that varies in permeability from one portion to another. For example, a permeability/blocking member and/or chamber can have a decrease in permeability from the upper surface to a lower portion, such that larger molecules can permeate the upper part with limited or no entry into the lower portion, but smaller molecules such as sodium and hydrogen ions can permeate the lower portion. This could be accomplished changing the relative amounts of the polymers, cross-linking agents, and/or photoinitiators that are used or deposited in the formation of the component. Alternatively, a permeability gradient may be accomplished by provided a permeability/blocking member that is thinner at the center than at the outer edge, or thinner at one side than at another side.

Some sensors may have a single continuous chamber. For example, FIG. 1d illustrates a sensor with a round body 203, a single chamber 207, and control elements 299. Control elements such as control elements 299 may have any suitable shape, size, color, or location, and may be provided on any component or portion of an implantable sensor (e.g., to a base/body, chamber, permeability/blocking member, and/or any other component). Examples of possible control elements include a fixed color and/or shape.

Other sensors may have multiple chambers and/or analysis regions in various arrangements, such as wedges (see e.g., FIG. 1e), rings, or other patterns. For example, a round sensor may have two or more analysis regions arranged in concentric rings. The inner ring may be configured to exhibit a response to an analyte concentration that is within a first range, and the second ring may be configured to exhibit a response to an analyte concentration that is within a second range. Alternatively, one or both of the rings may be configured for use as a control region and/or for detecting a non-target analyte.

Examples of Analyte Reagent Systems and Components

As discussed above, an analyte reagent system may include an indicator that provides a color change in response to a target analyte. An indicator may be, but is not limited to, a pH-sensitive dye with one or more chromoionophores, lipophilic anions, and/or ionophores. Other indicators may include luminescent reagents, enzymes, and/or reaction products.

Examples of chromoionophores include, but are not limited to: chromoionophore I (9-(diethylamino)-5-(octadecanoylimino)-5H-benzo[a]phenoxazine) designated ETH5249; chromoionophore II (9-dimethylamino-5-[4-(16-butyl-2,14-dioxo-3,15 ioxaeicosyl)phenylimino]benzo[a] phenoxazine) designated ETH2439; chromoionophore III (9-(diethylamino)-5-[(2-octyldecyl)imino]benzo[a] phenoxazine), designated ETH 5350; chromoionophore IV (5-octadecanoyloxy-2-(4-nitrophenylazo)phenol), designated ETH2412; chromoionophore V (9-(diethylamino)-5-(2-naphthoylimino)-5H-benzo[a]phenoxazine); chromoionophore VI (4',5'-dibromofluorescein octadecyl ester) designated ETH7075; chromoionophore XI (fluorescein octadecyl ester) designated ETH7061; and combinations thereof.

Examples of lipophilic anions include, but are not limited to: KTpClPB (potassium tetrakis(4-chlorophenyl)borate), NaHFPB (sodium tetrakis[3,5-bis(1,1,3,3,3-hexafluoro-2-methoxy-2-propyl)phenyl]borate), sodium tetrakis[3,5-bis (trifluoromethyl)phenyl]borate, sodium tetrakis(4-fluorophenyl)borate, combinations thereof, and the like.

Examples of ionophores include, but are not limited to: Sodium ionophores, such as bis[(12-crown-4)methyl]2-dodecyl-2-methylmalonate, designated ETH227; N,N',N''-triheptyl-N,N',N''-trimethyl-4,4',4''-propylidynetris(3-oxobutyramide), designated ETH157; N,N'-dibenzyl-N,N'-diphenyl-1,2-phenylenedioxydiacetamide, designated ETH2120; N,N,N',N'-tetracyclohexyl-1,2-phenylenedioxydiacetamide, designated ETH4120; 4-octadecanoyloxymethyl-N,N,N',N'-tetracyclohexyl-1,2-phenylenedioxydiacetamide), designated DD-16-C-5; 2, 3:11,12-didecalino-16-crown-5), bis(benzo-15-crown-5), and combinations thereof; Potassium ionophores, such as: bis[(benzo-15-crown-5)-4'-methyl]pimelate, designated BME 44; 2-dodecyl-2-methyl-1,3-propanedil bis[N-{5'-nitro(benzo-15-crown-5)-4'-yl]carbamate], designated ETH1001; and combinations thereof; Calcium ionophores, such as: (−)-(R, R)—N,N'-bis-[11-(ethoxycarbonyl)undecyl]-N,N'-4,5-tetramethyl-3,6-dioxaoctane-diamide), designated ETH129; N,N,N',N'-tetracyclohexyl-3-oxapentanediamide, designated ETH5234; N,N-dicyclohexyl-N',N'-dioctadecyl-3-oxapentanediamide), designated K23E1; 10,19-bis[(octadecylcarbamoyl)methoxyacetyl]-1,4,7,13,16-pentaoxa-10,19-diazacycloheneicosane), and combinations thereof.

FIG. 3 illustrates an example of a reagent system with a pH-sensitive indicator for use in an implantable sensor. This reagent system provides a GOx/pH based reaction that produces a color shift (i.e., a variation in reflected wavelengths of light) that can be measured to determine a glucose concentration. In this example, the chromoionophore is chromionophore III, the ionophore is bis[(12-crown-4) methyl]2-dodecyl-2-methylmalonate, and the lipophilic anion is sodium tetrakis[3,5-bis(1,1,3,3,3-hexafluoro-2-methoxy-2-propyl)phenyl]borate trihydrate. In this system, the chromoionophore exhibits a pH-dependent color between the extremes of orange and blue. The pH shifts in response to varying concentrations of glucose. The reflected wavelengths (orange, yellow, green, blue) from the analysis regions can be detected and analyzed to determine the local glucose concentration.

As illustrated, glucose and oxygen enter chamber 107 through permeability/blocking membrane (109/123). Chamber 107 may include an indicator coupled to a substrate 131. In the illustrated example, the indicator includes a chromoionophore 143, an ionophore 145, and a lipophilic anion 141. A detection reagent (e.g., GOx) may be immobilized on a substrate 135. Each of substrates 131 and 135 may be an independent component such as a bead, a membrane, a fiber, or a surface of body 105 that is exposed within chamber 107. In other examples, a substrate 131 and a substrate 135 may integrated within one component.

The GOx converts glucose and oxygen to gluconic acid and hydrogen peroxide. Increasing production of gluconic acid causes a shift in pH. The chromoionophore 143 accepts a hydrogen ion, which causes a shift in the color of the chromoionophore 143 toward blue. As electrical neutrality is maintained by the lipophilic anion 141, the ionophore 145 responds to the acceptance of the hydrogen ion by releasing a sodium ion to maintain the charge balance. As the production of gluconic acid decreases, the ionophore accepts a sodium ion, and the chromoionophore releases a hydrogen ion, causing a shift in color of the chromoionophore toward orange. The shift in color causes a corresponding shift in wavelengths reflected by the analysis regions, which can be detected to monitor glucose levels at desired time intervals.

Optionally, one or more additional reagents may be provided within chamber 107. The additional reagent(s) may be provided to increase the rate of a chemical reaction, stabilize one or more components of the analyte reagent system, and/or convert a reaction product to another product. For example, catalase may be provided to convert hydrogen peroxide to water and oxygen.

In some embodiments, sensor reagents of an analyte system may be segregated within chamber 107. This may be useful where two or more sensor reagents are incompatible or require different pH levels for optimal enzyme activity or stability. For example, within chamber 107, one or more pH sensing areas with an indicator may be segregated from one or more enzyme areas with detection reagents. The sensor reagents may be deposited separately in the respective areas, such as in one or more gels or on separate substrates. The respective areas may be in direct contact. Alternatively, another substrate or material may provide a transition zone between the areas. For example, a detection reagent such as GOx may be deposited in a first (enzyme) area and an indicator may be deposited in a second (pH sensing) area. Hydrogen ions generated in the reaction area would diffuse to the pH sensing area. Optionally, the hydrogen ions may diffuse through a hydrogel disposed between the two areas.

Some ESRD analyte sensors may include analysis regions configured to detect creatinine, urea and/or potassium. For example, an analysis region configured to detect urea may include urease and one or more pH sensing reagents (e.g., a pH-sensitive dye as described herein). In this example, urea is detected in a two stage reaction. In the first stage of the reaction, urea diffuses into the analysis region and is converted into ammonia and carbon dioxide by urease:

$$H_2O+(NH_2)_2CO=2NH_3+CO_2$$

In the second stage of the reaction, the ammonia generated in the first stage of the reaction causes an increase in pH, and the pH sensing reagents exhibit a response to the increase in pH in proportion to the level/concentration of urea.

In some embodiments, an analysis region configured to detect creatinine may include creatinine deaminase and one or more pH sensing reagents. In this example, creatinine is detected in a two stage reaction. In the first stage of the reaction, creatinine diffuses into the analysis region and is converted into methylhydantoin and ammonia by creatinine deaminase:

$$H_2O+creatinine=methylhydantoin+NH_3.$$

In the second stage of the reaction, the ammonia generated in the first stage of the reaction causes an increase in pH that is detected in the same way as described above with reference to urea detection.

In some embodiments, an analysis region configured to detect potassium may include 1,2-dimethyl-3-nitrobenzyene, potassium ionophore I, potassium tetrakis(4-chlorophenyl)borate, and sebacic acid dibutylester.

Optionally, some or all of the potassium-detecting reagents may be arranged in association with a membrane to form a potassium-sensing analysis region. In some embodiments, a creatinine-detecting analysis region and/or a urea-detecting analysis region may comprise a hydrogel. For example, the hydrogel may be positioned between the pH detection reagent(s) and the urease/creatinine deaminase. Optionally, the pH detection reagent(s) may be coupled with a membrane, the urease/creatinine deaminase may be coupled with another membrane, and the membranes may be positioned on opposing surfaces of the hydrogel.

While some implantable sensors may have two or more separate areas as described above, other sensors may have a plurality of similar but smaller micro-areas dispersed throughout a chamber 107 or along a permeability/blocking member in one or more patterns. Examples of suitable patterns include, but are not limited to, alternating dots/squares/lines and concentric circles. In a specific example, two respective areas are arranged to form two or more separate, concentric circular portions, with one of the areas (e.g., an enzyme area) disposed in an outer ring and surrounding the other area (e.g., a pH-sensing area).

Examples of ESRD Monitoring Systems and Reader Devices

Figure 4A:
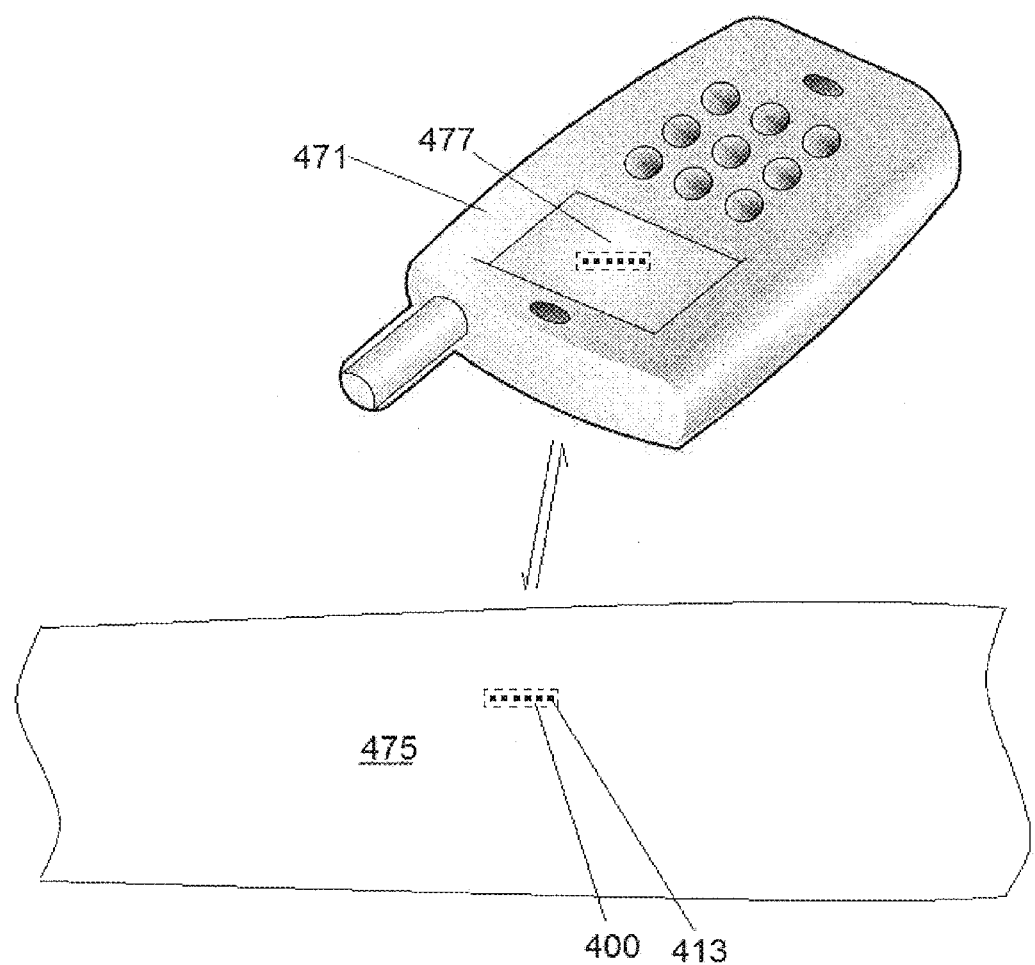
FIGS. 4a-f illustrate various aspects of an example of an ESRD analyte monitoring system.
Figure 4B:
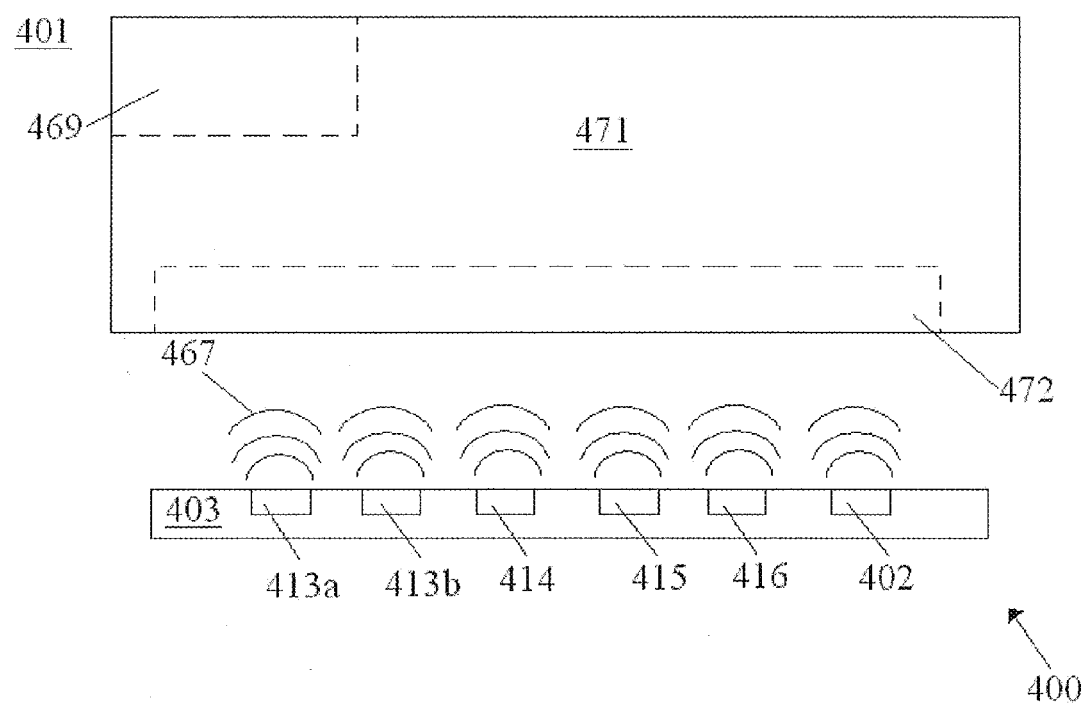
Figure 4C:
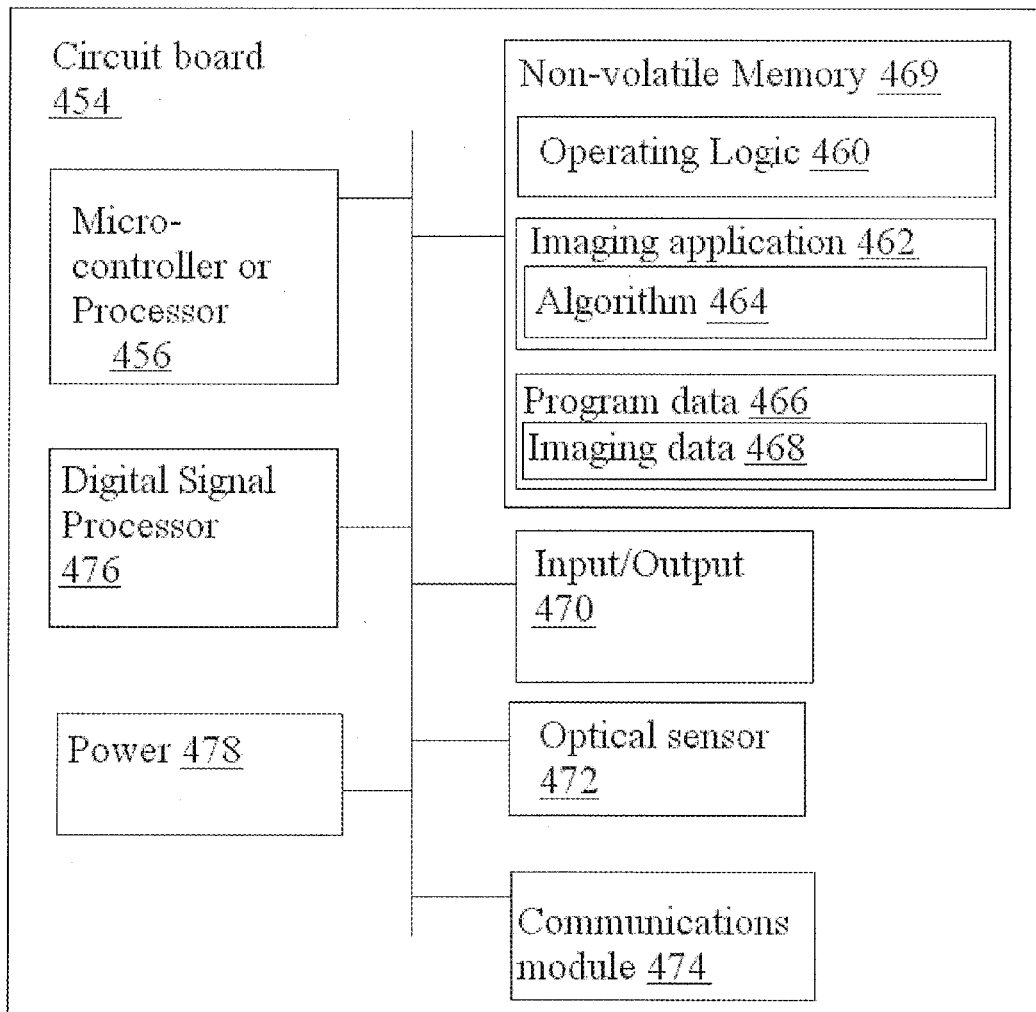
Figure 4D:
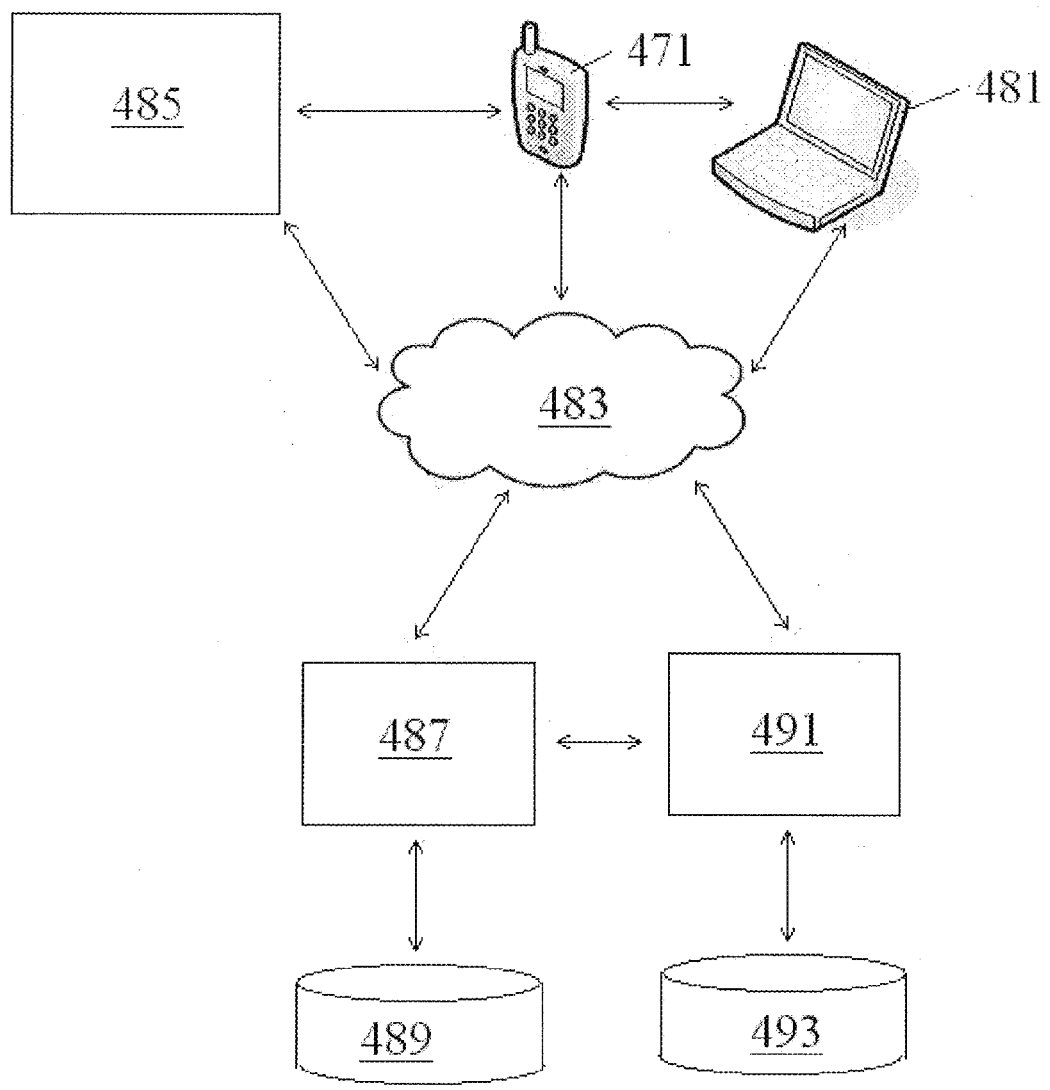
Figure 4E:
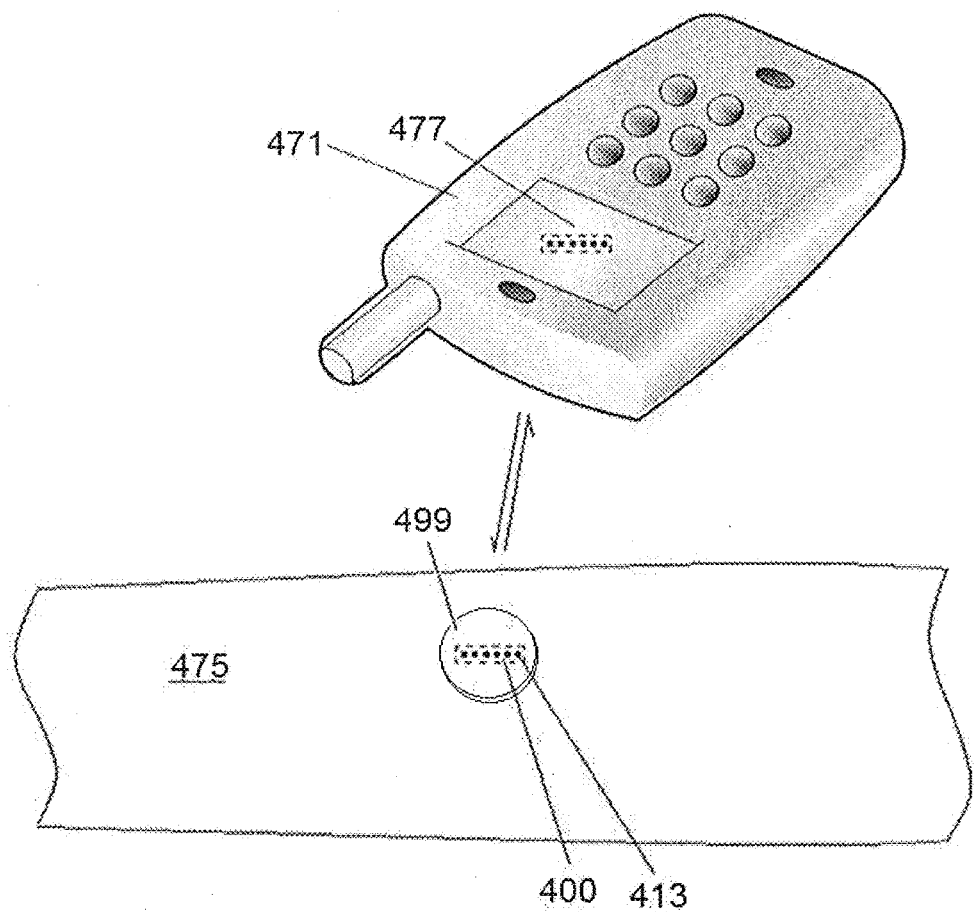

FIGS. 4a-f illustrate examples of mobile analyte monitoring systems and components thereof, in accordance with various embodiments. FIG. 4a illustrates the use of a reader device (e.g., electronic device 471) to capture an image of an implantable sensor 400 (shown implanted into a portion of the user's dermis 475). FIG. 4b shows a box diagram of a reader device and implantable sensor. FIG. 4c illustrates a circuit board of a cell phone configured for use as a reader device. FIG. 4d illustrates an example of a mobile analyte monitoring system that includes one or more additional computing devices, as discussed further below. FIG. 4e illustrates another embodiment of a mobile analyte monitoring system in which a reader device includes an electronic device 471 and a separate image capture device 499.

Examples of reader devices include, but are not limited to, personal electronic devices such as cell phones, smart phones, personal digital assistants (PDAs), tablet computers, laptop computers, media players, and other such devices. In particular embodiments, a reader device or a component thereof (e.g., image capture device 499) may be a mobile electronic device.

A reader device may be a single device, as described further below and illustrated by way of example in FIG. 4a. Alternatively, a reader device may include two or more devices communicatively coupled, as illustrated by way of example in FIGS. 4e and 4f. Therefore, in some embodiments, a "reader device" may include two or more electronic devices, and operations described and attributed herein to a reader device may be performed collectively by the two or more electronic devices.

In some embodiments, a reader device can include both a personal electronic device (shown in FIGS. 4a and 4e as 471) and an image capture device (shown in FIGS. 4e and 4f as 499) that is configured to be worn on, or otherwise attached to, a user's body (e.g., on an area of skin overlying an implantable sensor) during use. For example, image capture device 499 may be retained on the skin of the user over a sensor implantation site by an adhesive between the skin and the image capture device 499. Alternatively, image capture device 499 may be retained on the skin over a sensor implantation site by a belt, a band (e.g., worn in the manner of a wristwatch or armband), or an adhesive layer disposed over the image capture device 499 and portions of the surrounding skin. In one embodiment, image capture device 499 may have a clear or translucent portion (e.g., along the outer periphery) to allow light to pass through to the underlying analyte sensor. Alternatively, image capture device 499 may include a LED light or other light source that can be used to illuminate an underlying implanted analyte sensor. The LED light or other light source may be selectively illuminated at times that coincide with the capture of analyte sensor images by image capture device 499. In other embodiments, the LED/light source may remain continuously illuminated.

In various embodiments, the image capture device 499 may be configured to communicate data to a mobile electronic device such as a smartphone or a cell phone, or to another type of electronic device. The image capture device 499 and the personal electronic device 471 may each be configured to perform some of the reader device functions described throughout the present disclosure.

Figure 4F:
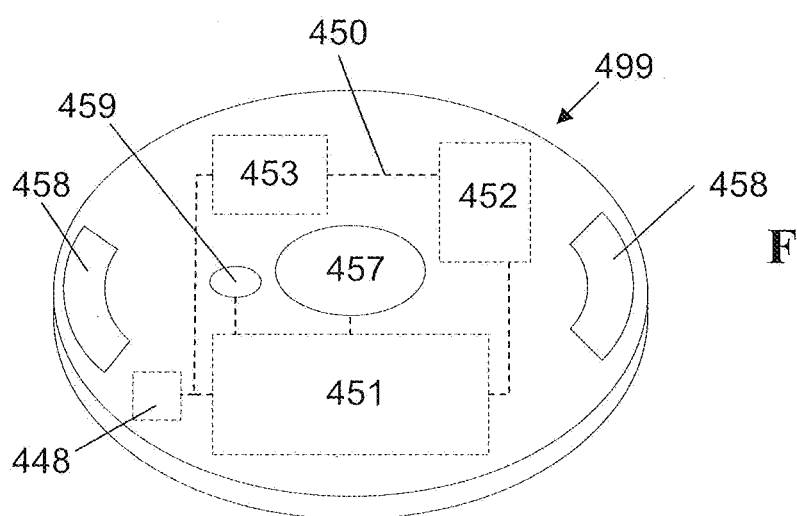

In a specific example, image capture device 499 may include one or more of a processor 451, an optical sensor 457, a memory 452, and a communications module 453 (e.g., a transmitter, transceiver, or other type of communications device) coupled by circuitry 450 (FIG. 4f). Optionally, image capture device 499 may include a power source 448 (e.g., a rechargeable battery or a replaceable battery). In some embodiments, image capture device 499 may be provided with an adhesive 458 for attaching the image capture device to the skin of the user. Optionally, image capture device 499 may include a light source 459, such as a LED light.

The electronic device 471 may be configured to receive images from the attached device and to perform some or all of the other processing and/or communications functions described herein for reader devices. The image capture device 499 may be configured to capture images continuously, at predetermined intervals (e.g., every 10 seconds), and/or in response to a command from another device or system (e.g., electronic device 471, a manufacturer's computing system, a health management system, etc.). Image capture device may be operable to transfer captured images of the analyte sensor to electronic device 471 for analysis. Optionally, the image capture device 499 may be configured to perform a rudimentary image analysis to determine whether the captured image is satisfactory, and/or to transmit image data to the cell phone or other electronic device for analysis/further transmission.

The reader device may thus collect, analyze, generate, and/or communicate analyte data or other health parameter data without requiring the intervention of the user to capture images of the implanted analyte sensor. Image capture device 499 and electronic device 471 may be used in a variety of circumstances, such as for analyte monitoring while the user is asleep, for closely monitoring users who are brittle diabetics and/or have relatively large target analyte fluctuations requiring close monitoring, for greater convenience to the user (e.g., to get continuous results without requiring the user to manipulate the reader device in order to capture analyte sensor images), or to provide continuous data for controlling a medical device such a dialysis machine and/or an insulin or glucagon pump/delivery system. In a particular example, the image capture device 499 may be ≤5 inch in width/diameter or 0.5-1.0 inch in width/diameter, and ≤25 inches thick.

Referring to FIG. 4c, a reader device may be a wireless mobile phone with one or more of the following features: circuit board 454, microcontroller or processor 456, digital signal processor 476, power module 478, non-volatile memory 469, input/output 470, optical sensor 472, and communications module 474. Communications module 474 can include a RF transmitter/receiver. Optionally, communications module 474 may also be configured to transmit and/or receive infrared (IR) or other signals.

Optical sensor 473 may be configured to detect electromagnetic radiation 467 that is reflected, deflected, and/or emitted from sensor 400. Optical sensor 473 may be any type of image capture device suitable for use in a personal electronic device. Optical sensor 473 can be, but is not limited to, a charge-coupled device (CCD) image sensor, a complementary metal-oxide-semiconductor (CMOS) image sensor, a CCD/CMOS hybrid sensor (e.g., sCMOS sensor), a Bayer sensor, a Foveon X3 sensor, a 3CCD sensor, and an active-pixel sensor (APS). Optionally, optical sensor 473 may be provided with one or more color filters, which may be removable/interchangeable.

Non-volatile memory 469 may include operating logic 460 (e.g., an operating system), imaging application 462, and program data 466. Imaging application 462 may include programming instructions providing logic to implement image analysis functionalities described herein. Program data 466 may include imaging data 468, as well as reference tables/values, reference images, previously determined representative values, and/or other data. Such data may be provided or stored using any suitable data structure or format. Examples include, but are not limited to, a lookup table, an array, an associative array, or a linked/unsorted list. FIG. 8 illustrates an example of a reference table that provides reference ranges for a target analyte (e.g., creatinine reference ranges) by age and gender. This reference table is provided merely by way of illustration, and is not intended to be limiting. The actual data structure, format, reference values, data type combinations, and other features may vary among embodiments. Some reference ranges may be ranges for a given analyte in interstitial fluid. Such ranges may be the same as, or different from, reference ranges for the same analyte in blood, plasma, or serum. Optionally, program data 466 may include an algorithm, table, or conversion factor for estimating a blood/plasma/serum concentration of the analyte based on the calculated representative value for that analyte. In other examples, reference ranges or other data may be provided as colors or color values, or luminescence/light emission values. Imaging data 468 may include previously captured images of implantable sensor 400 or corresponding image data.

Imaging application 462 can include one or more algorithms 464 for image analysis, calculation of representative values for analytes, tracking of representative values over time, analysis of a user's medication, and/or other functions. For example, imaging application 462 may include an algorithm 464 configured to analyze the effect of a user's medication based user inputs (e.g., times and dosages at which a medication was taken) and the determined concentrations of the medication or a related analyte at particular time points. Optionally, imaging application 462 may track the effect of the medication as a function of dosage and/or time, or suggest modifications in the dosage of the medication based on the analysis.

Microcontroller or processor 456 may be configured to operate optical sensor 472 and to execute operating logic 460, including imaging application 462. Operating logic 460 may include an operating system (OS). Input/output 470 may be configured to generate input signals in response to a user selection of a control, such as a keypad key or touchscreen/touchpad. Communications module 474 may be configured to transmit and receive communication signals for a call/audio message, an email message, and/or a text message. Communications module 474 may be a radio frequency transceiver, and may support one or more of any of the known signaling protocols, including but not limited to CDMA, TDMA, GSM, and so forth. Except for the manner in which any of the illustrated features, such as microcontroller or processor 456, are used in support of image capture/analysis functionalities as described herein, these features may otherwise perform their conventional functions as known in the art.

Referring now to FIGS. 4a and 4b, implantable sensor 400 may include one or more analysis regions 413a, 413b, 414, 415, 416, and a control region 402. The analysis regions and control region may be configured to analytes within a given concentration range (i.e., the detection range), as discussed above. A user may hold reader device 471 near the area of dermis 475 where implantable sensor 400 is located, and operate reader device 471 to capture an image of that area using optical sensor 473. Reader device 471 may execute imaging application 462 to determine the concentrations of the analytes in the interstitial fluid based at least on the captured image.

Optionally, the reader device may be configured to access a look-up table from program data 466 or a database (see e.g., FIG. 4d, databases 489/493) that stores one or more of a pre-determined pattern, reference image(s), and/or ranges for some or all of the pre-determined analysis regions. The reader device may determine or calculate a representative value for an analyte based on the image data and stored data. In some examples, the reader device may select an analysis region that differs from a pre-determined pattern in size/area, contour, and/or location. The reader device may extrapolate a detection range for this analysis region based at least on the difference(s) between the selected and pre-determined pattern, and corresponding detection range(s) provided in the look-up table or database.

Determined or calculated concentrations/representative values, captured image, image data, and/or other relevant data (e.g. time, date, identity of analyte, etc.) may be stored in non-volatile memory 469 as program data or imaging data. Reader device 471 may track the concentrations/representative values over time, recording them in a table or other format that can be displayed or communicated to the user. Optionally, reader device 471 may display the captured image and/or determined representative value on a display 477, communicate the results to the user or to another device/system, and/or generate and communicate a message, notification, alert, instructions, or a representative value (e.g., a target analyte concentration, a temperature, a pressure, etc.) to a user of the reader device in a visual, audio, and/or tactile (e.g., vibratory) format. In some examples, the reader device may alert the user of a possible sensor malfunction, or that the sensor is approaching or has reached or exceeded the end of its recommended duration of use.

In some embodiments, the reader device may transmit a message, notification, alert, instructions, or a representative value (e.g., a target analyte concentration, a temperature, a pressure, etc.) to a medical services provider or caretaker. As shown in FIG. 4d, reader device 417 may be communicatively coupled to one or more computing devices or systems via a wireless connection or network. Reader device 417 may exchange data with one or more of a personal computer 481, a network 483, a medical device 485, a first computing system 487, a first database 489, a second computing system 491, and/or a second database 493. In some examples, first computing system/database 487/489 may be a medical provider or health monitoring computing system/database, and may be operated or accessible by a first medical provider, such as a primary care physician of the user. Second computing system/database 491/493 may be operated by a caretaker or a second medical provider such as a doctor's office, hospital, emergency medical service, or subscription-based service that notifies a medical provider of a potential emergency. Alternatively, second computing system/database 491/493 may be a computing system/database of a manufacturer of a sensor that can be read by reader device 471 (e.g., an implantable sensor). As described further below, the computing system of the manufacturer may analyze or track data received from the reader device to assess sensor performance. Medical device 485 may include an insulin pump that is worn by the user or implanted into the user's body. Alternatively, medical device 485 may include a dialysis machine.

Figure 5:
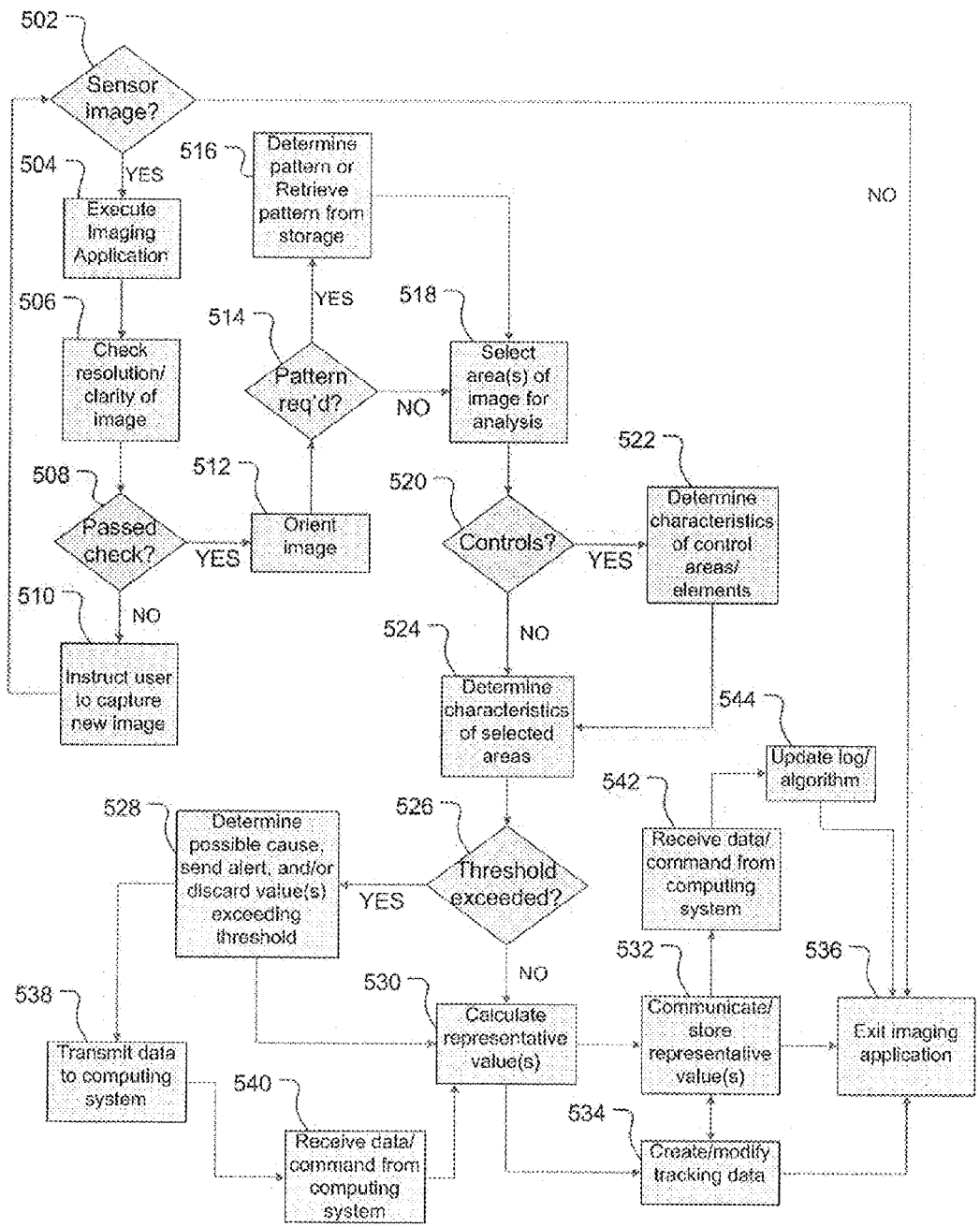
FIG. 5 illustrates an example of a logic flow diagram for an ESRD analyte monitoring system.
Figure 6:
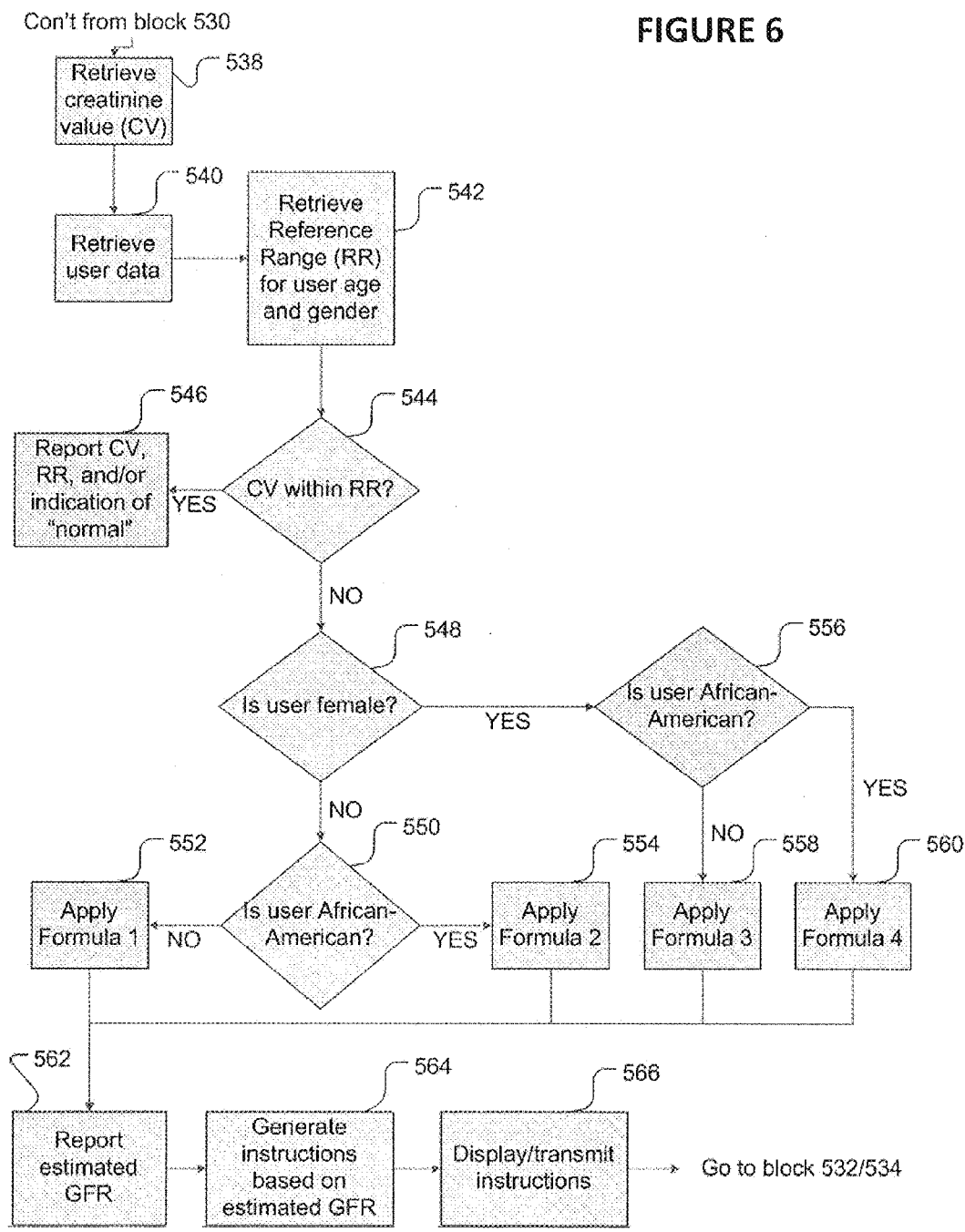
FIG. 6 illustrates an example of a logic flow diagram for determining an estimated glomerular filtration rate (eGFR)

FIGS. 5 and 6 illustrate a non-limiting example of a logic flow diagram for a reader device in an ESRD monitoring system, in accordance with various embodiments. Image analysis processes, tasks/steps, sequential orders in which steps/tasks are performed, and distribution of analysis tasks among the reader device and other devices/computing systems may vary among embodiments. Many variations and modifications to the illustrated logic flow will be readily understood by persons with ordinary skill in the art in light of the present disclosure, which encompasses all such variations and modifications.

Imaging application 462 is one example of an application suitable for use with a mobile analyte monitoring system. As used herein, the term "imaging application" refers to a program that directs a processor to perform various tasks related to analyte monitoring (e.g., image analysis, calibration, tracking of data, etc.). Imaging applications and operations thereof may vary among embodiments. Optionally, an imaging application may include, or may be provided with, reference data such as reference tables/values, reference images, and/or other relevant data (e.g., program data 466). Some imaging applications may be developed or configured for use with a particular type of reader device (e.g., a smartphone or tablet computer) and/or operating system (e.g., Google Android, Apple iOS, Nokia Symbian, RIM BlackBerry OS, Samsung Bada, Microsoft Windows Phone, Hewlett-Packard webOS, Linux operating system). Again, these examples are provided merely by way of illustration, and imaging applications may be configured/adapted/developed for use with many other types of reader devices (e.g., tablet computer, personal digital assistant, camera) and/or operating systems. Some imaging applications may be "cross-platform" applications developed or configured for use with multiple types of reader devices/operating systems. In some embodiments, a reader device may an iPhone or an iPad.

In some embodiments, an imaging application may be pre-installed on the reader device (e.g., by the reader device manufacturer). In other embodiments, the application may be provided in a physical medium, such as an optical disc (e.g., a CD, a DVD), a data storage disk (e.g., a ZIP disk), a flash memory device (e.g., a USB flash drive, a memory card), and the like. Alternatively, the application may be downloaded/electronically transmitted to the reader device or associated computer system (e.g., the user's personal computer) over a network (e.g., the Internet). The application may be made available for download from a computer system or database of a third party (e.g., a manufacturer of the sensor, a manufacturer of the reader device, a medical service provider, a software developer, a software distributor, or a web-based application store, such as the Apple App Store). In some embodiments, the imaging application may be a web-based application that resides on a server of the third party and is accessible by the reader device via the Internet (e.g., as a web application). In one example, a portion of the web-based imaging application may be downloaded to the reader device and may reside on the reader device thereafter. Alternatively, a portion of the imaging application may be downloaded to the reader device each time the reader device accesses/uses the imaging application.

In addition, although the reader device is typically used to capture images of the sensor, one or more of the other functions described herein as being performed by the reader device may instead be performed by another device or system, such as a computer, database, medical device, etc., and vice versa. For example, the reader device may capture an image of the sensor and transmit the image data to a computing system for analysis. Alternatively, image analysis functions may be divided among the reader device and another device or computing system. For example, the reader device may be configured to determine a representative value for a target analyte and the computing system may be configured to track the representative values over time and/or to generate and send instructions to the reader device to adjust one or more operational parameters (e.g., to adjust a setting of the optical sensor, to capture another image, or to set a time at which another image should be captured).

In addition, in some embodiments an analyte sensor may be read by a user without the use of a reader device. For example, the user may determine an approximate analyte concentration by viewing the analyte sensor without the aid of a reader device. Optionally, the user may be provided with a visual aid such as a chart, color key, or the like. The user may compare the response(s) of the analysis region(s) to the chart to determine an approximate analyte concentration. Alternatively, the user may interpret the response(s) of the analysis region(s) without the use of a visual aid. For example, after a period of time, the user may have sufficient experience with the use of the sensor to correlate the visible color change to an approximate analyte concentration. As another example, an analyte sensor may have multiple analysis regions that are configured to exhibit responses to the same analyte, but have different ranges of detection, such that at a given analyte concentration at least one of the analysis regions exhibits minimal or no color change. Based on which of the analysis regions displays a response, the user may determine that the analyte concentration is within a particular range.

Referring first to FIG. 5, the illustrated logic may optionally begin at block 502. At block 502, the reader device may determine whether a captured image is an image of an implantable sensor. In some examples, the determination may be based on an image recognition/matching process as is known in the art for machine recognition of human faces, structures, or items. In other examples, the determination may be based on input entered into the user device by a user, such as a user selection of a physical or virtual key, a button, an icon, or item on a displayed list. In still other examples, the reader device may determine that a captured image is an image of an implantable sensor in response to determining that a filter has been coupled to or engaged within the optical sensor of the reader device. In some embodiments the reader device may determine that a filter or lens has been attached to the optical sensor/reader device, or that a filter or lens is needed to improve or ensure image quality. Optionally, the reader device may instruct the user to attach a filter/lens, and/or confirm that the filter/lens has been attached properly such that the user can proceed to capture the image of the analyte sensor. Alternatively, second computing system/database 491/493 may be a computing system/database of a manufacturer of a sensor that can be read by reader device 471 (e.g., an implantable sensor). As described further below, the computing system of the manufacturer may analyze or track data received from the reader device to assess sensor performance.

Some embodiments may lack a block 502, and may execute the imaging application either automatically (e.g., in response to activation/use of the optical sensor) or upon receiving an input by the user to display/execute the imaging application or some portion thereof.

At block 504, the reader device may execute the imaging application (e.g., imaging application 462) in response to user input, a determination that a captured image is an image of an implantable sensor, or other factor (e.g., a pre-determined time for capturing an image of the implantable sensor, a received command from a remote device/computing system of a caretaker or medical care provider, etc.). Optionally, block 504 may include a calibration process by which the reader device is calibrated based on a target analyte concentration obtained by one or more other methods. For example, the reader device may be calibrated by determining a reference analyte concentration for one or more of the target analytes (e.g., urea, creatinine, potassium) by another method, such as a blood test at a medical facility, and inputting the reference analyte concentration(s) into the reader device. An image of the implanted analyte sensor may be captured and correlated to the reference analyte concentration(s) to calibrate the reader.

Optionally, at block 506, the reader device may check the captured image to determine whether the quality of the image is sufficient for analysis. This may be based on one or more pre-determined thresholds or limits for resolution, brightness/contrast, exposure/dynamic range, one or more settings or operation parameters of the optical sensor (e.g., shutter speed, exposure setting, Exposure Value Compensation setting), or other factors. If the reader device determines at block 508 that the quality of the image is insufficient for analysis, the reader device may communicate an instruction to the user to capture another image of the implantable sensor (block 510). The instruction may include a recommendation for the image capture, such as a recommended adjustment or setting for the optical sensor or a distance at which the optical sensor should be held from the implantable sensor for image capture. Optionally, the reader device may be configured to indicate whether one or more conditions (e.g., a current position or orientation of the reader device, lighting conditions, or a distance of the reader device from the sensor), is acceptable for capturing an image of the sensor, based at least on a bar code or other identifiers provided on the sensor. If the reader device determines that the quality of the image is sufficient for analysis, the logic may proceed to block 512.

At block 512, the reader device may orient the image. In some examples, this may involve rotating, resizing, and/or centering the image. In some embodiments, the reader device may orient the image according to one or more control elements that are located on or within the sensor (see e.g., FIG. 1d, control elements 299). For example, the reader device may orient an image of the sensor of FIG. 1d by aligning the four illustrated control elements 299 against a pre-determined pattern, a previous image, or pre-determined shape (e.g., four opposite corners of a square, or the top, bottom, left, and right sides of a square). Optionally, the reader device may use a bar code or other identifier of the sensor to retrieve calibration data from a computing system, network, or cloud. The reader device may thus orient the image based on the bar code or other identifiers.

Optionally, the reader device may determine that a pattern is required to orient or analyze the captured image (block 514), and may retrieve the pattern from local storage (e.g., program data 466 or imaging data 468) or from a remote database (block 516). In some examples, block 514 may be absent, and the reader device may automatically retrieve a pattern in block 512 for orientation of the image, orient the image without a pattern (e.g., by way of reference to control elements, other features of the sensor, or implantation site), or proceed without orienting the image.

At block 518, the reader device may select one or more areas of the image for analysis. The reader device may select portions of the captured image that correspond to analysis regions (e.g., analysis regions 413) based on color, intensity of emission, distance from the center/edge of the base/body or other feature, location on the sensor, prior readings, programmed instructions, and/or a pre-determined pattern or reference image. For example, the reader device may select areas of a captured or real-time image based at least on a pre-determined pattern (e.g., a layout of the analysis regions/ chambers of the implantable sensor). In other examples, the reader device may select areas based on position/distance relative to one or more control elements. Optionally, the reader device may increase or decrease the size of a selected area based on image resolution (e.g., select a larger area where image resolution falls below a minimum threshold).

At block 520, the reader device may select one or more areas of the image for use as controls. Optionally, the reader device may determine whether or not control areas should be selected for analysis, based on factors such as image quality and pre-stored information about the implantable sensor. In other embodiments, the reader device may select control areas in block 518 before, during, or after the selection of areas for analysis (e.g., areas corresponding to analysis regions). In any case, selected control areas may correspond to control regions (e.g., duplicate analysis regions configured to detect the same analyte within the same detection range, or analysis regions configured to detect non-target analytes or other parameters), control elements, other features of the sensor, and/or features of the overlying or proximal dermis or implantation site. Again, the selection of control areas may be based on a pre-determined pattern or any of the other factors described above with regard to selection of analysis areas.

Optionally, at block 522, the reader device may determine one or more characteristics of the selected control areas of the captured image before proceeding to block 524, in which other selected areas are analyzed (e.g., areas corresponding to analysis regions configured to detect the target analyte(s)). In other embodiments, blocks 522 and 524 may be reversed in order. In still other embodiments, blocks 522 and 524 may be combined into a single block. In any case, the determined characteristics of the selected control areas may include, but are not limited to, a color value, an intensity/brightness value, a size/dimension or position/orientation value, and/or a value representing a difference between any of the above values and a threshold or reference value.

At block 524, the reader device may determine one or more characteristics of one or more remaining selected areas of the captured image. Again, the determined characteristics may include, but are not limited to, a color value, an intensity/brightness value, a size/dimension or position/orientation value, and/or a value representing a difference between any of the above values and a threshold or reference value.

In some embodiments, these values may be calculated based at least in part on the values determined in block 522. For example, the reader device may determine at block 522 a value that represents a difference between the color of a control element (e.g., a colored spot) prior to implantation of the sensor and the color of the control element in the image of the implanted sensor (i.e., a "post-implantation color change" value). This value may be used in the determination of a color value of an analysis region to correct for, or minimize the effect of, factors such as implantation depth, skin tone, dermal translucence, lighting conditions, and/or others.

In some embodiments, one or more of the values determined for a control area may be used in the determination or correction of a value for another control area. Continuing the above example, a value that represents a difference between the color of the control element before and after implantation may be used to determine or correct a color value for a selected control area that corresponds to a control region configured to detect a non-target analyte. The non-target analyte may be one that is typically present at relatively constant levels within the dermis (e.g., sodium, chloride, or cholesterol). The reader device may determine a color value for the corresponding area of the image and adjust the color value based on the post-implantation color change value to correct for, or minimize the effect of, skin tone and other factors as discussed above.

Optionally, at block 526 the reader device may compare one or more of the determined values to one or more threshold values and determine whether any of the determined values exceed the threshold value(s). A threshold value may be, for example, an upper or lower limit of a pre-determined range of values, a determined value of a control region or analysis region, or an upper or lower limit of a range of values determined by the reader device based at least in part on one of the other determined values (e.g., a range of values representing the determined value of a control area and higher/lower values within a pre-determined margin of error). In some examples, the reader device may retrieve a standard or customized set of threshold values from a local or remote storage. In other examples, the reader device may determine the threshold values based on one or more previous readings. The reader device may apply different threshold values to at least some of the determined values. For example, the reader device apply a first set of threshold values to a value determined for an area corresponding to a potassium-detecting analysis region, and apply a second set of threshold values to a value determined for an area corresponding to a control element such as a colored spot. The reader device may also apply a set of control values to more than one determined threshold value (e.g., a maximum intensity threshold, above which results may be unreliable).

If the reader device determines that one or more of the determined values exceeds an applied threshold value, the reader device may generate a response at block 528. Examples of responses include determining a possible cause for the difference, sending an alert (e.g., to a user, a caretaker, a medical provider, etc.), transmitting data to a network, system, or remote computer/database, and/or discarding the value(s) that exceeded the applicable threshold. Determining a possible cause may include actions such as accessing prior readings from a memory/storage, checking one or more settings of the optical sensor, assessing the number or percentage of determined values that exceed the corresponding thresholds, or checking a reader device log for system errors. Sending an alert may include actions such as communicating an auditory (e.g., ring tone or alarm tone), vibratory, and/or visible message (e.g., text, email, display, or light activation) to the user, a caretaker, or a medical facility. Optionally, an alert may be sent to a medical device, such as an insulin pump, in the form of an instruction or command to adjust the operation of the medical device.

In some embodiments, the reader device may transmit image data, determined characteristics/values, or other relevant data to a network, system, or remote computer/database (block 538). For example, the reader device may transmit such data to a computing system of the sensor manufacturer. The computing system of the manufacturer may remotely monitor sensor performance in this manner, using data received from the reader device to analyze and track sensor performance characteristics for quality control purposes.

As another example, the reader device may transmit data to a remote computing system (e.g., of a healthcare professional or health/ESRD management system). The remote computing system may generate and send data, a command, a message for the user, and/or a message or alert for another entity (e.g., a caretaker or physician) to the reader device at block 540. For example, the remote computing system may determine based on the received data that the user (i.e., the sensor wearer) has analyte concentrations that necessitate a dialysis treatment within a particular time frame (e.g., 1 day, three days, one week, two weeks, or one month). In response, the remote computing system may transmit to the reader device a message for the user (e.g., "You must have a dialysis treatment no later than Friday," "You are in need of an immediate dialysis treatment," or "Your analyte concentrations indicate that you are in Stage 3 of renal disease—no dialysis required at this time").

Optionally, at block 540, the reader device may receive data and/or a command from the computing system of the manufacturer. The data/command may be an update to the reader device or medical device (e.g., an update to an algorithm), or an alert for the user with regard to the functionality of the device. For example, the received data/command may be a message instructing the user to recalibrate the sensor (e.g., with another testing method, such as conventional glucose strips to check glucose levels) or advising the user that the sensor should be replaced within a particular timeframe. As another example, the data may include a revised or updated algorithm configured to offset the effects of sensor deterioration/wear/aging (i.e., to offset a reduction in the magnitude or degree of the sensor's exhibited response to an analyte concentration as the sensor ages). In some examples, the computing system of the manufacturer may use data from one or more sensors to determine a projected useful life of a sensor, such as 30, 60, 90, 180, or more than 180 days.

In some embodiments, the data may include a command for a medical device. For instance, a dialysis machine may be communicatively coupled to the reader device, which may also be in communication with a remote computing system (e.g., of a medical device manufacturer). The remote computing system may receive and analyze the received data while the user is undergoing a dialysis treatment. In real time, the remote computing system may assess the effect of the dialysis on the user based at least on the image data and/or representative values of one or more analytes detected by the sensor. In response, the remote computing system may determine whether the user requires additional or continued dialysis, and under what condition(s). In this manner, the user's dialysis procedure can be closely monitored and fine-tuned to meet the needs of the individual. The received command/data may include an instruction to start, stop, or alter the dialysis process (e.g., increase or decrease flow rate). The received command/data may be received by the reader and transmitted directly or indirectly to the dialysis system. Alternatively, the command/data may be transmitted directly to the dialysis system and/or to another computing system, such as a healthcare provider computing system. The dialysis system can thus be adjusted incrementally to customize the treatment to the user.

At block 530, the reader device may determine a representative value for an area of the image corresponding to a portion of an analysis/control region. The determination may be based at least in part on the value determined for that area in block 522/524. In some embodiments, the value determined may be averaged with one or more other values (e.g., averaging determined values for duplicate or triplicate analysis regions, or averaging multiple determined values for different areas of the same analysis region).

To determine the representative value, the reader device may first determine the identity of the target analyte and the detection range of the corresponding portion of the analysis/control region. These values may be stored locally or remotely in the form of a look-up table or other record. In some examples, the reader device may refer to a pre-programmed sensor layout in order to determine a detection range for an area based on its position relative to one or more of control elements, the center or edge of the sensor, and/or another feature of the sensor.

In some examples, a look-up table/record or portion thereof may include representative values for each analysis area and/or portion of the implantable sensor. The data may be organized in various ways, such as in a single table for the entire sensor or in separate tables for each analyte/detection range. In any case, the look-up table/record(s) may have a list of possible color values, intensity values, or sub-ranges of such values, each associated with a corresponding representative value. Thus, the reader device may determine the representative value by accessing the record/table (or portion thereof) for the relevant portion of the implantable sensor, locating the color value/intensity/sub-range that matches or most nearly matches the determined value, and retrieving the representative value associated with that color value/intensity/sub-range.

Alternatively, the reader device may be provided with a formula for calculating a representative value for a given area of the image. This may be done, for example, to adjust the representative value based on one or more of the control area/element values. A different formula may be provided for each analyte/detection range or combinations thereof, or for each analysis region of the sensor. The relevant formula (s) may be stored locally or remotely, and accessed by the reader device as needed.

Calculating a representative value may include comparing the representative value to one or more reference values. Some reference values may be pre-determined, such as a glucose range or a creatinine range. Other reference values may be representative values of a control area. For example, a selected area may correspond to a control region configured to detect a non-target analyte typically present at relatively constant levels within the dermis (e.g., sodium, chloride, or cholesterol) or a local condition (e.g., pH). The reader device may determine a representative value for the non-target analyte or condition, and compare the representative value to an expected range of values. If a difference between the reading and the reference values is determined to exceed a margin of error, the reader device may respond by adjusting one or more representative values (e.g., creatinine values) as a function of the difference. Alternatively, the reader device may determine that the reading is inaccurate and disregard it, determine that the sensor is malfunctioning, and/or send an alert as discussed with regard to block 528.

Optionally, the reader device may compare determined values and/or representative values for two, three, or more than three selected areas of the image to determine whether a portion of the sensor is exhibiting a response that is inconsistent with the response of another portion of the sensor. The inconsistency may be, for example, a difference in response time, a difference in color, or a difference in intensity. The reader device may use the comparison to determine that the sensor is leaking or otherwise malfunctioning, determine a time frame for replacement of the sensor, or engage in error correction or data smoothing to determine a representative value. Optionally, the reader device may determine that a response or value from a region exceeds a predetermined threshold/value, differs from an average or other selected value by more than a predetermined limit, or is outside a particular range, such as an expected range. In response, the reader device may disregard that response or value when determining a representative value for the target analyte (or non-target control analyte).

Some control regions may be duplicates of analysis regions, configured to detect the same target analyte within the same range of detection and response. The reader device may compare the responses of the two regions and determine whether the responses are the same within a margin of error. If a difference between the responses is determined to exceed the margin of error, the reader device may determine that the sensor is malfunctioning, alert the sensor user, and/or disregard one or both responses. Alternatively, the reader device may average the responses from the two regions and determine a representative value for the target analyte (or non-target control analyte) based on the determined average.

Some analysis/control regions may be used by the reader device to correct or determine representative values for a target analyte based on a local condition such as local blood/fluid flow, or changes/differences in analyte diffusion rates. For example, a control region may be configured to detect an analyte that is administered to an animal. Optionally, the analyte may be administered to the animal simultaneously or contemporaneously with a dose of a drug, a treatment, or a target analyte. The reader device may determine the time at which the analyte is administered. The reader device may read the response(s) of the control region at pre-determined times, at timed intervals, or continuously. The reader device may then correct or determine a representative value for a non-target analyte as a function of the length of time between the administration of the drug/treatment and the detection of the analyte by the control region. Optionally, the reader device may determine that the length of time exceeds a predetermined limit and alert the sensor user or reader device user of a condition such as poor circulation or possible sensor malfunction.

The response time may be used to calibrate the reader device or adjust one or more representative values. For example, the reader device or a computing system may determine a sensor lag time based on the response time. The sensor lag time can be a difference between the length of time required for the sensor to detect an analyte (e.g., a drug, treatment, or other analyte) or analyte concentration change in the dermis and the length of time required for the analyte to be detected in an analysis of whole blood, plasma, or other fluid(s). The reader device may then adjust one or more of the representative values to correct for the lag time. In some examples, the reader device may be programmed to remind a user to capture an image of the sensor at particular times or intervals. The sensor lag time may be used by the reader device to adjust those times or intervals.

At blocks 532 and 534, the reader device may optionally communicate/store the representative values and/or create/modify tracking data, respectively, as discussed above. In one embodiment, reader device 471 may be configured to compare the representative value to a reference range (see e.g., FIG. 8) or predetermined threshold. The reader device may determine that the representative value is above or below the predetermined threshold, or falls outside the reference range. The reader device may respond by alerting the user and/or transmitting the representative value to a computing system or device of a medical care provider or caretaker. The receiving computing system or device may be programmed to respond by generating and sending a communication to the user (e.g., a phone call, text message, email message, etc.) to check the result using a different device or system, such as a blood glucose meter or a laboratory blood test.

Optionally, at block 532 the reader device may communicate calculated values and/or other data to another computing system, such as computing system of a sensor/device manufacturer as described above with regard to block 538. At block 542, the reader device may receive data from the computing system, and may update a log and/or algorithm at block 544 as described with regard to block 540.

In another embodiment, at block 532 the reader device may communicate calculated values and/or instructions to a medical device. For example, the medical device may be a dialysis machine, and the reader device may transmit one or more of the representative values to the dialysis machine or to a medical care provider operating the dialysis machine. Optionally, the reader device may generate and transmit one or more instructions to the dialysis machine to stop, start, continue operating, or alter the rate of fluid flow. Alternatively, the dialysis machine may be programmed to adjust one or more operating parameters based on a representative value or other data received from the reader device. In some embodiments, the medical device may include a glucagon delivery system. The medical device may ping the reader device for data at timed intervals or in response to an event (e.g., input from user or medical care provider system, or based on an algorithm of the medical device). In some examples, the medical device or a computing system of a medical care provider or sensor manufacturer may prompt the reader device to take a new reading of the sensor, or alert the user to take a new reading of the sensor. Alternatively, the computing system of a medical care provider or sensor manufacturer may send data to the medical device indicating a need for a particular number of readings at particular intervals/times, and the medical device may request the readings/data from the reader device or send a message to the reader device reminding the user to capture images of the sensor at those intervals/times. Interactions between the reader device, medical device, and a computing system are further described in FIGS. 7a-b and in the accompanying description below.

At block 536, the reader device may exit the imaging application.

In some embodiments, the reader device may perform additional calculations/determinations before exiting the application. For example, after calculating or determining the representative values of analytes at block 530, the reader device may determine or calculate one or more additional representative values based at least in part on a calculated/determined analyte concentration and additional data. The additional data may represent factors such as the user's age/birthdate, gender, ethnicity (e.g., Caucasian, African-American, etc.), weight, height, medications, or other information which may be input by the user or received/retrieved from a local or remote storage.

FIG. 6 illustrates an example of a logic flow diagram for determining an estimated glomerular filtration rate (eGFR). In this example, after the reader device determines a representative value for creatinine at block 530, the reader device may determine an estimated glomerular filtration rate (eGFR) based on the creatinine value, the user's age, the user's gender, and the user's ethnicity.

At blocks 538 and 540, the reader device may retrieve or access the creatinine representative value (CV) and the user data, respectively. Optionally, at block 542, the reader device may retrieve a reference range for the CV based on the user's age and gender. At block 544, the reader device may compare the CV and the reference range to determine whether the CV falls within the reference range. If so, the reader device may report the CV as normal, or within the reference range, and exit the eGFR determination process (e.g., return to block 532/534).

If the reader device determines that the CV is outside the reference range, the reader device may proceed to select, based on the user data, a formula for calculating eGFR (blocks 548-560). In this example, the basic formula is the MDRD study equation:

$$\text{GFR (mL/min/1.73 m}^2) = 186 \times (Pcr)^{-1.154} \times (\text{age})^{-0.206} \times (0.724 \text{ if female}) \times (1.212 \text{ if African American})$$

Therefore, based on user gender and ethnicity, the reader device may select one of the following:

$$\text{GFR (mL/min/1.73 m}^2) = 186 \times (Pcr)^{-1.154} \times (\text{age})^{-0.203} \quad \text{Formula 1(male=Caucasian):}$$

$$\text{GFR (mL/min/1.73 m}^2) = 186 \times (Pcr)^{-1.154} \times (\text{age})^{-0.203} \times (1.212) \quad \text{Formula 2(male=African American):}$$

$$\text{GFR (mL/min/1.73 m}^2) = 186 \times (Pcr)^{-1.154} \times (\text{age})^{-0.203} \times (0.742) \quad \text{Formula 1(female=Caucasian):}$$

$$\text{GFR (mL/min/1.73 m}^2) = 186 \times (Pcr)^{-1.154} \times (\text{age})^{-0.203} \times (0.724) \quad \text{Formula 2(female=African American):}$$

Alternatively, one or more other formulas may be used to calculate eGFR, estimated creatinine clearance rate (eCCr), and/or other values. Examples of other eGFR formulas that may be used include the CKD-EPI formula, the Mayo Quadratic formula, and the Schwartz formula. Some reader devices may be configured to select from among two or more methods of calculation based on various factors such as age. For example, the reader device may select the Schwartz formula for a user aged 12 years or less, and one of the other formulas for a user with an age of more than 12 years. As another example, the reader device may select the Mayo Quadratic formula instead of the MDRD formula to calculate eGFR based on a current or previous indication that the user is at an earlier stage of kidney disease or has relatively preserved kidney function (e.g., a creatinine representative value that falls within a standard range, or input by the user that the user is in stage 1-3).

The reader device may also compare the determined or calculated value to a reference range or reference values. For example, eGFR reference ranges may be provided for each stage of renal disease:

| Stage | eGFR value |
|---|---|
| 1 | 90 mL/min or more |
| 2 | 60-89 mL/min |
| 3 | 30-59 mL/min |
| 4 | 15-29 mL/min |
| 5 | Less than 15 mL/min (or on dialysis) |

At block 562, the reader device may report the determined or calculated value as previously discussed with regard to FIG. 5. Optionally, at blocks 564 and 566, the reader device may generate, display, and/or transmit instructions based on the determined or calculated value. The instructions may also be based at least in part on user data, prior values, or other data. For example, if the reader device determines that an eGFR value is lower than a previous eGFR value, the reader device may send an instruction to the user to make an appointment with a medical care provider. The reader device may also send an instruction to the medical care provider to follow up with the user. The logic may then proceed to block 532/534 or to another block.

Figure 7A:
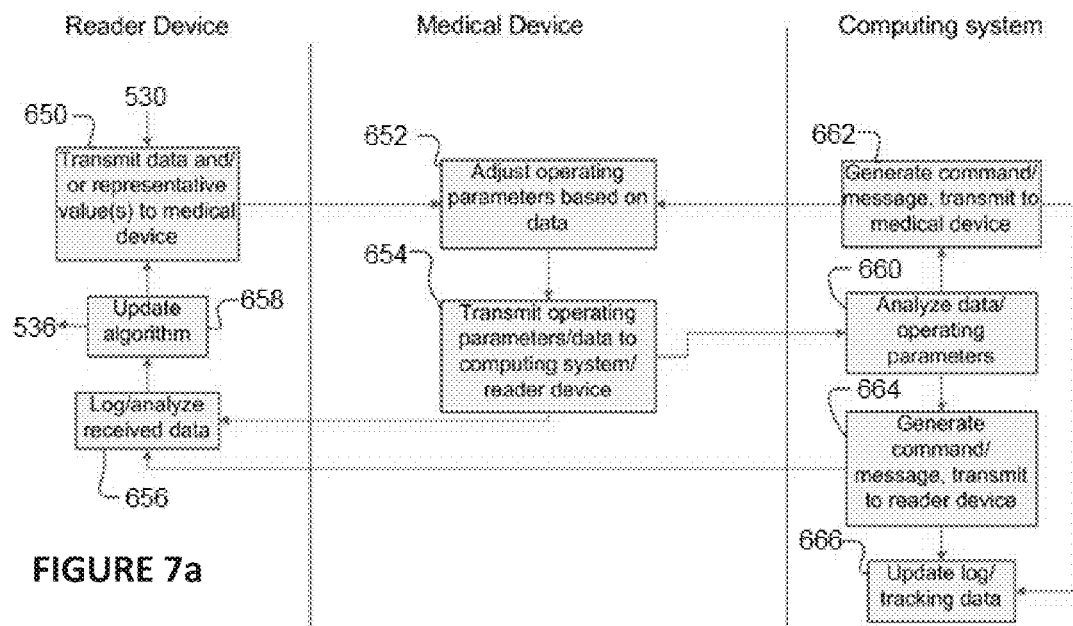
FIGS. 7a-b illustrate examples of logic flow diagrams for an ESRD analyte monitoring system.
Figure 7B:
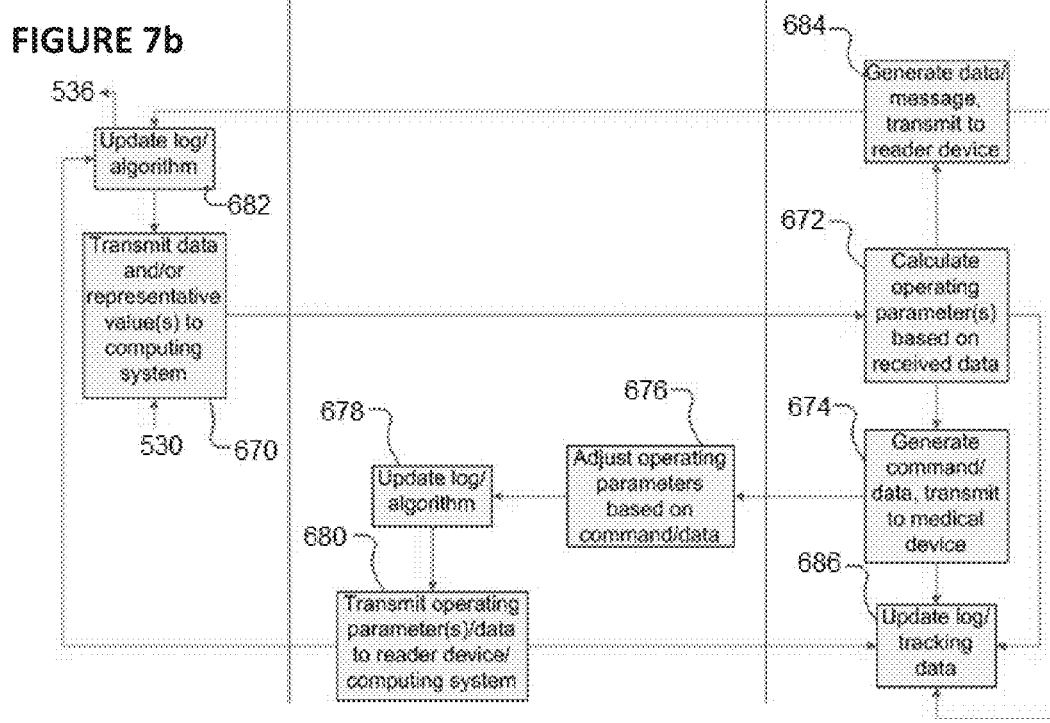

In some embodiments, a medical device may be partially or fully controlled by the reader device and/or a computing system in a closed-loop operation. Examples of such operations are illustrated in FIGS. 7a-b. These examples are provided by way of illustration and are not intended to be limiting. A person with ordinary skill in the art will readily understand many possible variations of these operations, all of which are intended to be encompassed within the present disclosure.

FIGS. 7a-b illustrate examples of logic flow diagrams for an ESRD analyte monitoring system. In FIGS. 7a-b, the medical device can be, but is not limited to, a dialysis machine, an insulin pump, and/or a glucagon delivery system. Operating parameters can include, but are not limited to, flow rate, change in flow rate, duration of flow/treatment, start, stop, time remaining before start/stop, power on, power off, display of a message or data, detected error(s), or various other actions performed by a medical device. In some examples, the medical device may include a non-volatile computer readable medium with one or more algorithms for determining adjustments to the operating parameters based on received data or values. The computing system can be, but is not limited to, a computing system of a medical provider, medical device manufacturer, sensor manufacturer, or health management system.

The reader device may send representative values or other data to the medical device and/or computing system. In some embodiments, the medical device and/or computing system may ping the reader device for data at timed intervals or in response to an event (e.g., input from user or computing system, or an algorithm of the medical device). In some examples, the medical device or computing system may prompt the reader device to take a new reading of the sensor, or alert the user to take a new reading of the sensor. Alternatively, the reader device or computing system may send data to the medical device indicating a need for a particular number of readings at particular intervals/times, and the medical device may respond by requesting the readings/data from the reader device at the specified intervals/times, or by sending a message to the reader device reminding the user to capture images of the sensor at those intervals/times. Optionally, the computing system, the medical device, and/or the reader device may store user data such as treatment protocols, physiological parameters (e.g., weight, height, gender, age, etc.), prior sensor readings, and/or prior treatment parameters, any or all of which may be used to fine-tune the operation of the medical device for the individual user.

FIG. 7a illustrates an embodiment in which any one or more of the reader device, the medical device, and the computing system are configured to control at least some operations of the medical device based at least on sensor readings. In this embodiment, representative values calculated by the reader device (block 530, FIG. 5) and/or other data may be transmitted by the reader device to the medical device (block 650). The medical device may adjust one or more of its operating parameters based on the received data/representative values (block 652). In some examples, the medical device may determine or calculate the adjustments based on the received data. In other examples, the reader device and/or the computing system may determine or calculate the adjustments and send one or more commands to the medical device to adjust the operating parameter(s).

Optionally, the medical device may transmit operating parameters or other data, such as an error code or a flow rate, to the reader device (block 654). The reader device may log and/or analyze the data (block 656). The analysis may be based at least in part on one or more recent sensor readings, a look-up table, a set of standard values, or other stored or received data. Based on the analysis, the reader device may determine additional changes to the operating parameter(s) of the medical device. For example, the reader device may determine, based on recent sensor readings/representative values, that the sensor user's monitored analyte concentrations are nearing target levels. The reader device may then determine, based in part on flow rate/duration data received from a dialysis machine, a reduced flow rate or anticipated duration for the dialysis treatment.

Optionally, the reader device may update one or more algorithms based at least on received data and/or analysis (block 658). The process may then proceed to block 650 again, and the reader device may transmit representative values and/or additional data (e.g., a command to stop or decrease flow rate) to the medical device. Thus, the reader device and medical device may form a closed-loop control system.

In some examples, the closed-loop control system may include a computing system that generates and transmits data, commands, and/or messages to the medical device, the reader device, or both. At block 654, the medical device may transmit operating parameters or other data (e.g., data received from the reader device) to the computing system. The computing system may analyze the received data (block 660). In some examples, the computing system may be a computing system of the manufacturer of the medical device, and the received data may be used to track the performance of the medical device.

Alternatively, the computing system may be a treatment management system configured to optimize treatments provided by the medical device for an individual user. For example, the computing system may compare the received data to stored values and parameters (e.g., from previous treatments of the same or other users) to determine an optimum flow rate and remaining duration of treatment. The computing system may then generate and transmit a command/message to the medical device at block 662, and the medical device may adjust one or more operating parameters based on the command/message (block 652). Optionally, the computing system may generate and transmit a command/message to the reader device (block 664). For example, the computing system may determine that the dialysis should be ended. The computing system may send a stop command to the dialysis machine and a message to the reader device for viewing by the user (e.g., "your dialysis treatment has ended"). Again, the reader device may receive and log/analyze data from the computing system at block 656. The reader device may determine, based on the received data or analysis, that the treatment has ended, and may then exit the process (block 536, FIG. 5).

FIG. 7b illustrates an embodiment in which the computing system performs the primary analysis and control functions. The reader device may transmit data and/or representative values to the computing system at block 670. The computing system may analyze the data and calculate/determine operating parameters for the medical device based at least on the analysis (block 672). The computing system may send a command to the medical device to adjust the operation of the medical device (block 674). In some examples, the computing system may also send data or a message for the user to the reader device (block 684). For example, the computing system may determine based on the received data that the sensor is beginning to deteriorate, and that the algorithm used by the reader device should be updated to compensate for the resulting changes in sensor readings. The reader device may update its log and/or algorithm(s) with the received data (block 682).

At block 676, the medical device may adjust its operation based on the commands/data received from the computing system. Optionally, the medical device may update a log and/or algorithm based on the received data (block 678) and/or transmit its operating parameters or other data to the reader device and/or computing system (block 680). The computing device may maintain and update one or more logs (block 686) to track the performance of the medical device, the sensor, and/or the reader device.

The reader device, computing system, and/or medical device may also send messages or updates to caretakers, medical care providers, a database, or other entities. For example, the computing system may send a message to the reader device for review by the user (e.g., "you must receive a dialysis treatment within the next 48 hours") and another message to a health care provider or facility (e.g., "Patient X requires a dialysis treatment within the next 48 hours"). In one example, the reader device or the health care provider/facility may respond by automatically accessing a scheduling function to schedule an appointment for the required treatment, by sending an alert to the user, or sending an alert to personnel of the healthcare provider. The reader device may optionally initiate an audio, vibratory, or visual alert at decreasing intervals until receiving an indication that the treatment has been scheduled and/or received.

Embodiments of systems, methods, and devices described herein may be used to monitor kidney function in a user after a kidney transplant. Typically, the recipient of a kidney transplant must be monitored closely by medical providers, especially within the first 30-45 days after the transplant. ESRD monitoring as described throughout the present disclosure may be used to monitor the user's renal function after the transplant, which may allow the user to return for followup care less frequently. ESRD monitoring may also be used to track the function of the transplanted kidney as the kidney becomes active and its functionality improves. Embodiments of systems, methods, and devices described herein may also be used to fine tune dialysis treatment parameters and/or to coordinate dialysis treatment centers with home dialysis operations.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. A closed loop renal function monitoring and dialysis control system, comprising:
   an analyte sensor, comprising:
      a base and plurality of analyte reagent systems coupled to the base, wherein the analyte reagent systems exhibit a reversible color change in response to a corresponding plurality of target analytes relevant to renal function wherein the plurality of target analytes comprise at least two or more of glucose, creatinine, urea, and potassium; and one or more control regions coupled to the base that detect a non-target analyte that is present at relatively constant levels within the dermis;
a reader device that captures an image of the analyte sensor;
a computing device communicatively coupled to the reader device, the computing device comprising:
a computer processor; and
a computer-readable storage device storing instructions executable by the computer processor for:
identifying the image as an image of the analyte sensor;
selecting one or more areas of the image for analysis;
selecting one or more areas of the image for use as controls; and
measuring a concentration for each of the plurality of target analytes relevant to renal function based on the one or more areas of the image selected for analysis; and
a hemodialysis machine communicatively coupled to the computing device, wherein the computer-readable storage device further comprises instructions executable by the computer processor for:
controlling operations of the hemodialysis machine in response to the measured concentrations of the plurality of target analytes relevant to renal function.

2. The system of claim 1, wherein the reader device is a mobile electronic device selected from the group consisting of a cell phone, a smart phone, a personal computer, and a personal digital assistant.

3. The system of claim 1, wherein the base comprises a polymeric material impregnated with $TiO_2$.

4. The system of claim 1, wherein the base is reflective and comprises a metal.

5. The system of claim 1, wherein the analyte sensor is insertable into an animal.

6. The system of claim 5, wherein the analyte sensor is insertable into the dermis of the animal.

7. The system of claim 6, wherein the animal is a human, the reader device comprises an image capture device and a smart phone in wireless communication with the image capture device, and the image capture device is configured to be retained on the animal's body proximal to the analyte sensor.

8. The system of claim 1, wherein the plurality of analyte reagent systems comprises one or more of a lipophilic anion, a chromoionophore, and an ionophore.

9. The system of claim 1, further comprising instructions executable by the computer processor for calculating an estimated glomerular filtration rate.

10. The system of claim 1, wherein the analyte sensor has a total thickness of 50 μm or less.

11. The system of claim 1, wherein the analyte sensor provides a qualitative indication of analyte concentration that is visible to the user.

12. The system of claim 1, wherein the reader device is part of the computing device.

13. A method of monitoring renal function and controlling a hemodialysis machine, the method comprising:
implanting an analyte sensor into the dermis of a subject with end stage renal disease, the analyte sensor comprising:
a base and plurality of analyte reagent systems coupled to the base that detect one or more analytes in the interstitial fluid of the individual relevant to renal function wherein the plurality of target analytes comprise at least two or more of glucose, creatinine, urea, and potassium; and
one or more control regions coupled to the base that detect a non-target analyte that is present at relatively constant levels within the dermis;
receiving a first image data representative of a first image of an analyte sensor;
identifying the image as an image of the analyte sensor;
selecting one or more analysis regions for analysis;
selecting one or more areas of the image for use as controls;
determining, based at least on the first image data, a first color value corresponding to a portion of the one or more analysis regions;
determining a concentration of the one or more analytes based at least on the first color value; and
controlling operations of a hemodialysis machine in response to the measured concentrations of the plurality of target analytes relevant to renal function.

14. The method of claim 13, wherein the reader device is a smart phone.

15. The method of claim 13, wherein said determining the concentration of the target analyte is performed by a third party computer system, the method further comprising communicating the concentration of the target analyte to the reader device.

16. The method of claim 15, further including determining, based at least on the concentration of the one or more analytes, a recommended time frame for the individual to begin dialysis treatment.

17. The method of claim 15, further comprising:
receiving additional image data representing subsequent images of the analyte sensor during a dialysis treatment administered to the individual with the dialysis machine;
analyzing the additional image data during the dialysis treatment; and
calculating one or more adjustments to the dialysis treatment based at least on the additional image data.

18. The method of claim 17, further comprising:
receiving second image data representative of a second image of the analyte sensor; and
analyzing one or more performance characteristics of the analyte sensor based at least on the first and second image data.

19. The method of claim 13, wherein the dialysis machine is a peritoneal dialysis machine.

20. The method of claim 13, wherein the individual is a kidney transplant recipient, the method further comprising:
receiving a plurality of additional image data representative of a corresponding plurality of images of the analyte sensor, wherein the plurality of images are captured over a period of time;
determining additional concentrations of the one or more analytes based at least on the plurality of additional image data; and
analyzing kidney function over the period of time based at least on the determined concentrations of the one or more analytes.

21. A non-transitory computer readable medium comprising instructions for a closed loop renal function monitoring and control system operable, upon execution by a processor of an electronic device, to cause the electronic device to:
receive an image of an analyte sensor that includes a plurality of analysis regions exhibiting reversible color changes in response to changes in concentrations of a corresponding plurality of target analytes, comprising two or more of creatinine, glucose urea, and potassium, and one or more control regions that detect a non-target analyte that is present at relatively constant levels within the dermis;

identify the image as an image of the analyte sensor;

select one or more areas of the image for analysis;

select one or more areas of the image for use as controls;

determine, based at least on the image, color values corresponding to each of said analysis regions;

determine concentrations of the target analytes based at least on the color values; and control operations of a hemodialysis machine in response to the measured concentrations of the plurality of target analytes relevant to renal function.

22. The non-transitory computer readable medium of claim 21, the instructions further operable, upon execution by the processor, to cause the electronic device to calculate an estimated glomerular filtration rate based at least on one or more of the determined concentrations of the target analytes.

23. The non-transitory computer readable medium of claim 21, the instructions are further operable, upon execution by the processor, to cause the electronic device to determine, based at least on one or more of the determined concentrations of the target analytes, a recommended time frame for a user of the analyte sensor to begin dialysis treatment based at least on the determined concentration.

24. The non-transitory computer readable medium of claim 21, wherein the instructions are further operable, upon execution by the processor, to cause the electronic device to:
receive additional images of the analyte sensor,
analyze the additional images during a dialysis treatment administered to the user with the dialysis machine; and
adjust the one or more operations of the dialysis machine based at least on the analysis of the additional images.

25. The non-transitory computer readable medium of claim 21, wherein the instructions are further operable, upon execution by upon execution by the processor, to cause the electronic device to:
receive a plurality of additional images of the analyte sensor; and
determine, based on the additional images, a recommended time frame for replacement of the analyte sensor.

26. The non-transitory computer readable medium of claim 21, wherein the instructions are further operable, upon execution by upon execution by the processor, to cause an optical sensor of the electronic device to capture the image of the analyte sensor.

* * * * *